(12) United States Patent
Krulevitch et al.

(10) Patent No.: US 8,556,866 B2
(45) Date of Patent: Oct. 15, 2013

(54) DRUG DELIVERY SYSTEM

(75) Inventors: Peter Krulevitch, Pleasanton, CA (US); Robert Wilk, Sierra Village, CA (US); Ulrich Kraft, Hofheim (DE); Donna Savage, Rolling Hills Estates, CA (US); Nick Foley, Edinburgh (GB); James Glencross, Edinburgh (GB); David Shepherd, Edinburgh (GB); Zara Sieh, San Ramon, CA (US)

(73) Assignee: LifeScan, Inc.

( * ) Notice: Subject to any disclaimer, the term of this patent is extended or adjusted under 35 U.S.C. 154(b) by 0 days.

(21) Appl. No.: 13/203,694

(22) PCT Filed: Jan. 27, 2010

(86) PCT No.: PCT/US2010/022241
§ 371 (c)(1),
(2), (4) Date: Sep. 8, 2011

(87) PCT Pub. No.: WO2010/098928
PCT Pub. Date: Sep. 2, 2010

(65) Prior Publication Data
US 2011/0313350 A1    Dec. 22, 2011

Related U.S. Application Data

(60) Provisional application No. 61/156,386, filed on Feb. 27, 2009, provisional application No. 61/156,421, filed on Feb. 27, 2009, provisional application No. 61/156,472, filed on Feb. 27, 2009, provisional application No. 61/164,250, filed on Mar. 27, 2009.

(51) Int. Cl.
*A61M 5/315* (2006.01)
*A61M 5/178* (2006.01)
*A61M 5/00* (2006.01)

(52) U.S. Cl.
USPC ............ 604/223; 604/227; 604/186; 604/246

(58) Field of Classification Search
USPC ......... 604/207–211, 223–224, 227–228, 181, 604/218, 186, 246, 65–76
See application file for complete search history.

(56) References Cited

U.S. PATENT DOCUMENTS

| 4,803,625 A | 2/1989 | Fu et al. |
| 4,950,246 A | 8/1990 | Muller |

(Continued)

FOREIGN PATENT DOCUMENTS

| EP | 1363224 A1 | 11/2003 |
| WO | WO 99/43283 A1 | 9/1999 |

(Continued)

OTHER PUBLICATIONS

M. Franetzki, et al., "Design and Data of a Compact Device for Sustained Program-Controlled Medicament Infusion" Hormone and Metabolic Research, Supplement Series (1982), 12 (Islet-Pancreas-Transplant. Artif. Pancreas), 169-172, ISSN: 0170-5903, ISBN: 086577062x.

(Continued)

*Primary Examiner* — Nicholas Lucchesi
*Assistant Examiner* — Rebecca E Eisenberg

(57) ABSTRACT

Various embodiments of a "smart" drug delivery system are provided which includes an add-on module and a reusable or disposable drug pen. Upon attachment to the pen, the add-on module may: determine dosage selected, injection of selected dosage, duration of injection, time of injection, whether the pen has been primed or shaken to thoroughly mix up insulin mixtures, transmit information relating to insulin dosage and injection to a data management unit, provide reminders, error warning or messages on improper usage or reusage of needles, track amount of drug remaining on board the pen or duration of usage of pen with respect to expiry of the drug on board, or provide an audible alarm for locating misplaced pen and module.

21 Claims, 22 Drawing Sheets

(56) References Cited

U.S. PATENT DOCUMENTS

| | | | |
|---|---|---|---|
| 4,995,402 A | 2/1991 | Smith et al. |
| 5,204,670 A | 4/1993 | Stinton |
| 5,216,597 A | 6/1993 | Beckers |
| 5,383,865 A | 1/1995 | Michael |
| 5,417,222 A | 5/1995 | Dempsey et al. |
| 5,536,249 A | 7/1996 | Castellano et al. |
| 5,558,638 A | 9/1996 | Evers et al. |
| 5,593,390 A | 1/1997 | Castellano et al. |
| 5,678,562 A | 10/1997 | Sellers |
| 5,728,074 A | 3/1998 | Castellano et al. |
| 5,820,602 A | 10/1998 | Kovelman et al. |
| 5,830,152 A | 11/1998 | Tao |
| 5,925,021 A | 7/1999 | Castellano et al. |
| 5,950,632 A | 9/1999 | Reber et al. |
| 5,957,896 A | 9/1999 | Bendek et al. |
| 6,024,699 A | 2/2000 | Surwit et al. |
| 6,038,676 A | 3/2000 | Yanes et al. |
| 6,134,504 A | 10/2000 | Douglas et al. |
| 6,144,922 A | 11/2000 | Douglas et al. |
| 6,192,891 B1 | 2/2001 | Gravel et al. |
| 6,235,004 B1 | 5/2001 | Steenfeldt-Jensen et al. |
| 6,270,455 B1 | 8/2001 | Brown |
| 6,277,099 B1 * | 8/2001 | Strowe et al. | 604/207 |
| 6,298,017 B1 | 10/2001 | Kulakowski et al. |
| 6,443,890 B1 | 9/2002 | Schulze et al. |
| 6,482,185 B1 | 11/2002 | Hartmann |
| 6,524,239 B1 | 2/2003 | Reed et al. |
| 6,540,672 B1 | 4/2003 | Simonsen et al. |
| 6,554,798 B1 | 4/2003 | Mann et al. |
| 6,585,698 B1 | 7/2003 | Packman et al. |
| 6,641,533 B2 | 11/2003 | Causey, III et al. |
| 6,790,178 B1 | 9/2004 | Mault et al. |
| 6,817,986 B2 | 11/2004 | Slate et al. |
| 6,869,413 B2 | 3/2005 | Langley et al. |
| 6,942,646 B2 | 9/2005 | Langley et al. |
| 7,169,132 B2 | 1/2007 | Bendek et al. |
| 7,397,730 B2 | 7/2008 | Skyggebjerg et al. |
| 7,427,275 B2 | 9/2008 | DeRuntz et al. |
| 7,713,229 B2 | 5/2010 | Veit et al. |
| 2002/0052578 A1 | 5/2002 | Moller |
| 2002/0126036 A1 | 9/2002 | Flaherty et al. |
| 2003/0005891 A1 | 1/2003 | Lu |
| 2003/0023203 A1 | 1/2003 | Lavi et al. |
| 2003/0038047 A1 | 2/2003 | Sleva et al. |
| 2003/0208113 A1 | 11/2003 | Mault et al. |
| 2003/0220814 A1 | 11/2003 | Gordon |
| 2004/0122355 A1 | 6/2004 | Langley et al. |
| 2005/0049179 A1 | 3/2005 | Davidson et al. |
| 2005/0182358 A1 | 8/2005 | Veit et al. |
| 2006/0153693 A1 | 7/2006 | Fiechter et al. |
| 2006/0173260 A1 * | 8/2006 | Gaoni et al. | 600/365 |
| 2006/0224123 A1 | 10/2006 | Friedeli et al. |
| 2007/0021715 A1 | 1/2007 | Kohlbrenner et al. |
| 2007/0060800 A1 | 3/2007 | Drinan et al. |
| 2007/0123829 A1 | 5/2007 | Atterbury et al. |
| 2007/0129708 A1 | 6/2007 | Edwards et al. |
| 2008/0099366 A1 | 5/2008 | Niemiec et al. |
| 2008/0188813 A1 | 8/2008 | Miller et al. |
| 2008/0208142 A1 | 8/2008 | Moller |
| 2008/0306434 A1 | 12/2008 | Dobbles et al. |
| 2008/0312605 A1 | 12/2008 | Saiki |
| 2009/0012479 A1 | 1/2009 | Moller et al. |
| 2009/0163793 A1 | 6/2009 | Koehler et al. |
| 2010/0286665 A1 * | 11/2010 | Manna et al. | 604/542 |

FOREIGN PATENT DOCUMENTS

| | | |
|---|---|---|
| WO | WO 02/062212 A3 | 8/2002 |
| WO | WO 03/005891 A1 | 1/2003 |
| WO | WO 03/047426 A1 | 6/2003 |
| WO | WO 2004/006785 A1 | 1/2004 |
| WO | WO 2006/075016 A1 | 7/2006 |

OTHER PUBLICATIONS

Lord, et al., "MiniMed Technologies Programmable Implantable Infusion Systyem," Annals of the New York Academy of Sciences, 1988;531:66-71.

Prestele, et al., "A Remote-Programmable Implantable Insulin Dosing Device Part 1" Techincal Concept and Features, Hormone and Metabolic Research, Supplement Series (1982), 12 (Islet-Pancreas-Transplant. Artif. Pancreas), 304-7, ISSN: 0170-5903, ISBN: 086577062x.

Christopher D. Saudek, "Development of Implantable Insulin Infusion Devices", Methods in Diabetes Research, vol. II: Clinical Methods, 1986, pp. 347-360, Editors Clarke, William; Larner, Joseph; et al.

HumaPen Memoir (revised Nov. 20, 2006) (retrieved from http:pi.lilly.com/us/memoir_user_manual.pdf accessed on Mar. 15, 2010).

The Smart Pen by John Walsh, May 18, 2008 (retrieved from http://challengediabetes.diabetech.net/2008/05/14the-smart-insulin-pen-by-john-walsh/ accessed on Mar. 15, 2010.

The Smart Pen by John Walsh, (retrieved from http://www.diabetesnet.com/diabetes_technology/smart_pen.php accessed on Mar. 15, 2010).

Chinese Patent Application No. 201080019326.9, Chinese First Office Action dated Feb. 6, 2013, 6 pages, State Intellectual Property Office, P.R. China.

European Patent Application No. 10746603.9, extended European search report dated Jan. 10, 2013, 8 pages, European Patent Office, Germany.

* cited by examiner

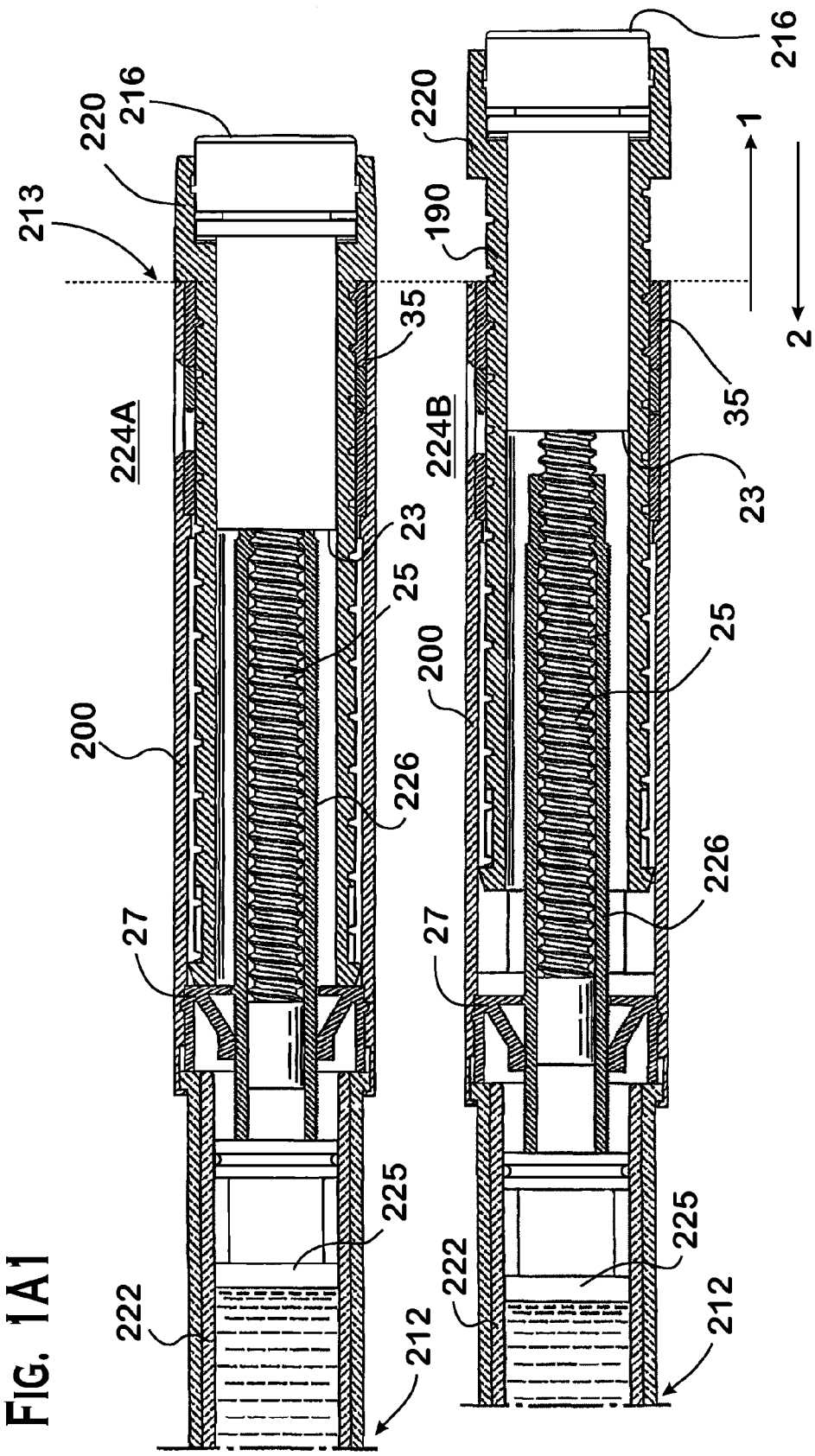

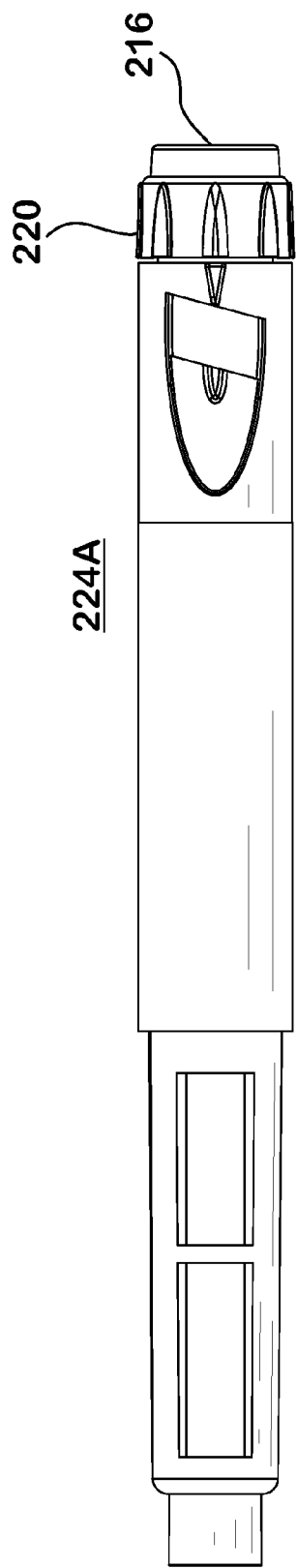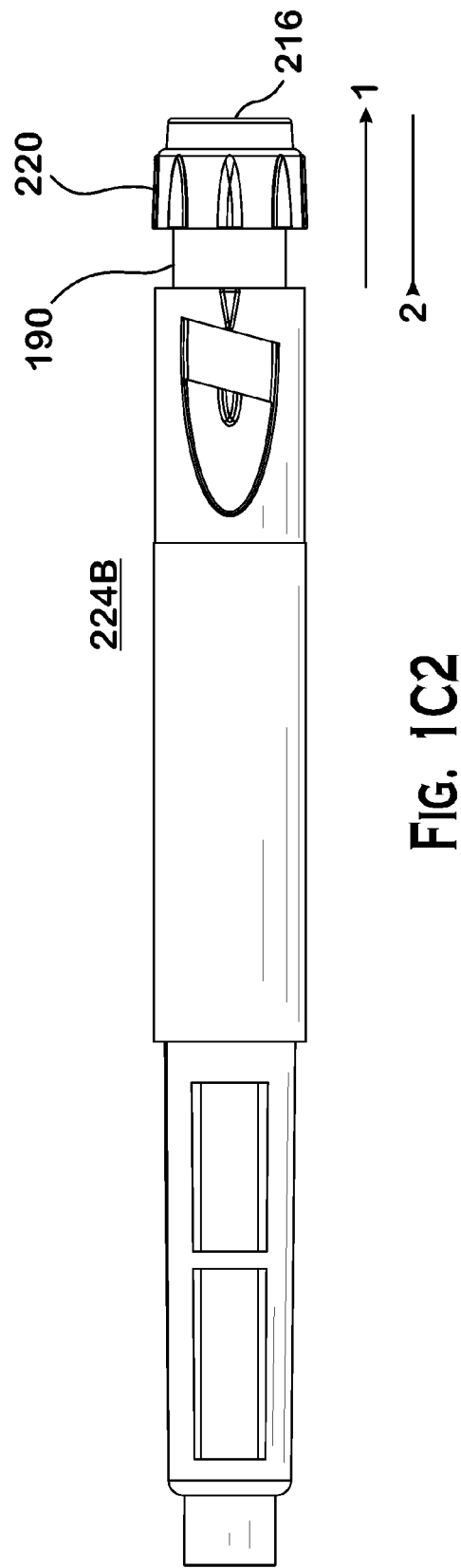
FIG. 1C1
FIG. 1C2

DRUG DELIVERY SYSTEM

PRIORITY

This application claims the benefits of priority under 35 USC§§120 and 371 of the following prior International Applications: (a) PCT/US2010/022236, filed Jan. 27, 2010, which claims the benefit of priority under 35 USC§119 to Provisional Patent Application Ser. No. 61/156,386, filed on Feb. 27, 2009, entitled "Medical Module for Drug Delivery Pen"; (b) PCT/US2010/022241, filed Jan. 27, 2010 (which claims the benefit of priority under 35 USC§119 to Provisional Patent Application Ser. No. 61/156,421, filed on Feb. 27, 2009, entitled "Drug Delivery System"; (c) PCT/US2010/022242, filed Jan. 27, 2010, which claims the benefit of priority under 35 USC§119 to Provisional Patent Application Ser. No. 61/156,472 filed on Feb. 27, 2009, entitled "Drug Delivery Management Systems and Methods"; (d) PCT/US2010/022245, filed Jan. 27, 2010 (which claims the benefit of priority under 35 USC§119 to Provisional Patent Application Ser. No. 61/164,250 filed on Mar. 27, 2009, entitled "DRUG DELIVERY MANAGEMENT SYSTEMS AND METHODS"), all of the listed prior applications are hereby incorporated by reference in their entirety herein.

BACKGROUND

It is believed that five million people worldwide, or approximately 56% of all insulin users, use insulin pens to inject their insulin. Insulin pens are convenient, easy to use, and discrete compared to syringes and vials, resulting in improved adherence and better outcomes. In addition, insulin pens reduce the time required for health care practitioners to initiate insulin therapy.

SUMMARY OF THE DISCLOSURE

Embodiments of the present invention address key issues, including: bringing together insulin therapy and blood glucose monitoring into more integrated therapeutic/monitoring systems; simplifying insulin initiation and intensification protocols; making blood glucose values central in the management of diabetes; and providing diabetes system solutions for improved outcomes and lower costs. The embodiments of the present invention help the patient and care provider stay on top of insulin therapy by automatically communicating delivered doses to a blood glucose meter, by recording the amount and time of insulin delivery, and by displaying a summary of a patient's blood glucose and insulin administration history. The embodiments of the present invention confirm whether the patient has already dosed, keeps track of the time and amount of insulin delivery, and eliminates the need to keep a manual logbook. Embodiments of the present invention help health care practitioners keep track of patient compliance.

Not only will embodiments of the invention facilitate management of diabetes, the invention and its embodiments will also be applicable in any field where drug delivery to a patient is utilized. For example, in the field of pain management or arthritis management, anxiety or epilepsy management (e.g., Diazepam) and the like.

In view of the foregoing and in accordance with one aspect of the present invention, there is provided a drug delivery system that includes a drug delivery pen and an add-on module. The drug delivery pen has a generally tubular pen housing that extends from a first end to a second end, the first end of the housing enclosing at least a portion of a plunger rod coupled to a drug cartridge disposed proximate the second end of the housing. The first end of the pen housing has a dosage selector coupled to the plunger rod. The add-on module housing extends along a first longitudinal axis from a first housing end to a second housing end. The add-on module housing includes first and second extensions that partially circumscribe a portion of the first end of the pen housing for attachment of the add-on module housing to the drug delivery pen.

In yet another embodiment, a drug delivery system is provided that includes a drug delivery pen and an add-on module. The drug delivery pen has a generally tubular pen housing that extends from a first end to a second end. The first end of the housing encloses a plunger rod coupled to a plunger disposed in a drug cartridge located proximate the second end of the housing. The first end of the pen housing has a dosage selector coupled to the plunger rod. The add-on module includes a primary communication module housing and a secondary module housing. The primary communication module housing extends along a first longitudinal axis from a first communication module housing end to a second communication module end. The secondary communication module housing is coupled to the primary housing module. The secondary communication module extends along a second axis to define at least a portion of a hollow bore. The at least a portion of a hollow bore is configured for attachment over an actuation unit of a drug delivery pen. The primary housing includes a dosage sensor, a follower portion connected to the dosage sensor and disposed for movement relative to the primary communication module housing, and retention forks connected to the follower portion, the retention forks configured to capture a button of the dosage selector between the retention forks.

In yet a further embodiment, a drug delivery system is provided that includes a drug delivery pen and an add-on module having a casing. The drug delivery pen has a generally tubular pen housing that extends from a first end to a second end, the first end of the housing enclosing at least a portion of a plunger rod coupled to a plunger disposed in a drug cartridge located proximate the second end of the housing. The first end of the pen housing has a dosage selector coupled to the plunger rod. The add-on module housing extends along a longitudinal axis from a first housing end to a second housing end to define at least a portion of a hollow bore in which the hollow bore is configured for attachment over at least a portion of the first end of the drug delivery pen. The casing is connected to the module housing and configured to enclose a portion of an outer surface of the module housing, the casing being located asymmetrically with respect to the longitudinal axis to house electrical components. The casing includes a dosage sensor disposed in the casing, follower portion physically connected to the dosage sensor and disposed for movement relative to the housing, and a knob mounted to the housing and physically connected to the dosage sensor via the follower portion so that a portion of the dosage sensor is movable in proportion to movement of the knob along the longitudinal axis.

In another embodiment, a drug delivery system is provided that includes a drug delivery pen and an add-on module having a casing. The drug delivery pen has a generally tubular pen housing that extends from a first end to a second end, the first end of the housing enclosing at least a portion of a plunger rod coupled to a plunger disposed in a drug cartridge located proximate the second end of the housing. The first end of the pen housing has a dosage selector coupled to the plunger rod. The add-on module is configured to attach to the drug delivery pen proximate the first end of the pen housing. The add-on module includes a module housing and a casing. The add-on module extends along a longitudinal axis from a first housing end to a second housing end to define at least a portion of a hollow bore disposed about the longitudinal axis in which the hollow bore is configured to couple over a portion of the first end of the pen housing. The casing is connected to the module housing to enclose a portion of an outer surface of the module housing. The casing includes means for determining either one of a dosage delivery or duration of dosage delivery or both upon actuation of the pen by a user.

In an alternative embodiment, a drug delivery system is provided that includes a drug delivery pen and an add-on module. The drug delivery pen has a generally tubular pen housing that extends from a first end to a second end, the first end of the housing enclosing at least a portion of a plunger rod coupled to a plunger disposed in a drug cartridge located proximate the second end of the housing. The first end of the pen housing has a dosage selector coupled to the plunger rod. The add-on module is configured to attach to the pen proximate the first end of the pen housing. The add-on module includes a housing extending along a longitudinal axis from a first housing end to a second housing end to define an internal surface of at least a portion of a hollow bore disposed about the longitudinal axis and means for measuring displacement of a dosage selector of the drug delivery pen. The internal surface defines the hollow bore capable of enclosing an outer surface of a drug delivery pen in one mode, and the internal surface of the hollow bore being visible to an observer in another mode when the housing is separated from the drug delivery pen.

In yet another embodiment, a drug delivery system is provided that includes a drug delivery pen and an add-on module. The drug delivery pen has a generally tubular pen housing that extends from a first end to a second end. The first end of the housing encloses a plunger rod coupled to a plunger disposed in a drug cartridge located proximate the second end of the housing. The first end of the pen housing has a dosage selector and dosage actuator coupled to the plunger rod. The add-on module is configured to attach to the pen proximate the first end of the pen housing. The add-on module includes a primary housing extending along a longitudinal axis from a first housing end to a second housing end to define an internal surface of at least a portion of a hollow bore disposed about the longitudinal axis and a dosage sensor. The internal surface defines the hollow bore capable of enclosing an outer surface of a drug delivery pen in one mode, and the internal surface of the hollow bore being visible to an observer in another mode when the housing is separated from the drug delivery pen. The secondary housing is disposed to cover a portion of the primary housing to enclose a portion of an outer surface of the primary housing. The dosage sensor is disposed in the secondary housing and configured to connect to the selector and dosage actuator of the drug delivery pen.

These and other embodiments, features and advantages will become apparent when taken with reference to the following more detailed description of the embodiments of the invention in conjunction with the accompanying drawings that are first briefly described.

BRIEF DESCRIPTION OF THE FIGURES

The accompanying drawings, which are incorporated herein and constitute part of this specification, illustrate presently preferred exemplary embodiments of the invention, and, together with the general description given above and the detailed description given below, serve to explain features of the invention (wherein like numerals represent like elements), of which:

FIGS. 1A1 and 1A2 illustrate cross-sectional side views of a drug delivery pen where a dosage selector is in an initial state and after a dosage setting has been set, according to an exemplary embodiment described and illustrated herein.

FIGS. 1C1 and 1C2 illustrate front views of a drug delivery pen module where a dosage selector is set to a zero dose and where the dosage selector has rotated such that a pen button has telescoped outwards, according to an exemplary embodiment described and illustrated herein.

FIG. 2 illustrates a front perspective view of the first type of medical module, according to an exemplary embodiment described and illustrated herein.

DETAILED DESCRIPTION OF THE FIGURES

Figure 1:
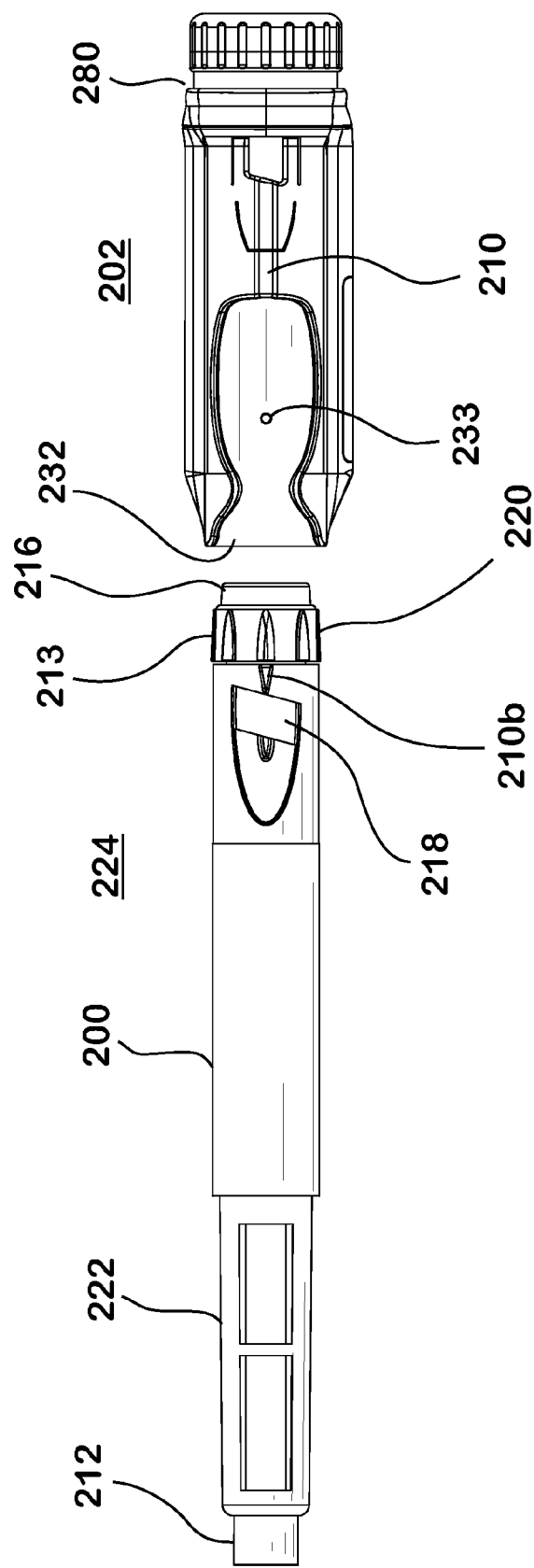
FIG. 1 illustrates a front view of a system that includes a drug delivery pen and a first type of medical module, according to an exemplary embodiment described and illustrated herein.

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

Insulin pens are commonly used as a simple, convenient, and effective technique for delivering insulin. Unlike syringes, which must be filled from a vial and require the user to estimate the dosage volume based on the position of a meniscus against a fine graduated scale, insulin pens are accurate and relatively easy to use. Insulin pens come in two basic types: (1) disposable pens that come pre-loaded with the insulin cartridge and are thrown away after the cartridge is empty, and (2) re-usable pens that require the user to load the insulin cartridges. Most insulin pens are purely mechanical, but there are versions on the market that have digital displays and record the most recent dosing history in memory (see, for example, the Humapen Memoir). To use a pen, the user attaches a needle, primes the device, dials in the desired dosage, inserts the needle subcutaneously, and then presses a button to inject.

Despite the simplicity and ease of use of insulin pens relative to syringes, applicants have recognized that there are aspects that may be improved. For example, applicants note that the typical disposable pens do not record insulin delivery events. This makes it difficult for the patient and their doctor to retrospectively analyze insulin delivery patterns and the relationship with blood glucose data. This is necessary to help the user and their doctor understand the relationship between blood glucose levels and insulin delivery in order to optimize insulin dosing. In addition, patients who have forgotten whether or not they have taken their insulin have no way to verify a delivery event. A missed injection may result in hyperglycemia (two missed bolus shots per week is known to raise HbA1C levels), and taking too much insulin could result in a life-threatening hypoglycemic event. While models such as the Humapen Memoir record the most recent injections in the pen memory, the insulin industry in some countries is moving away from durable pens in favor of disposables. In the pens that store data, it is not possible to download long-term data to study it in conjunction with blood glucose data. While others have speculated on so-called "smart pen" devices that incorporate wireless communication, for example "the Smart Insulin Pen" by John Walsh, P.A., C.D.E. (see, for example, http://www.diabetesnet.com/diabetes_technology/smart_pen.php), these are complex devices that are not consistent with the disposable pen model being adopted by the insulin companies. Finally, the regulatory pathway for approval of new pen devices is a long and expensive process.

Recognizing the shortcomings of the conventional insulin pens, applicants have invented various embodiments of a medical module that may be used not only with conventional insulin pens but also with any drug delivery pen. Various exemplary embodiments of the medical module are provided with useful features. For example, the communication modules are provided with dose sensing and wireless communication capabilities. The unit may be designed to work with various disposable drug delivery pens manufactured by the different insulin companies. The unit may be used in conjunction with pen devices for delivering medications other than insulin, such as, for example, growth hormone, GLP-1 analogs, Symlin, biologic molecules, and other injected biopharmaceuticals.

In the exemplary embodiments, the medical module is preferably a small, low profile, lightweight device that attaches to a disposable or reusable drug delivery device (e.g., an insulin pen) and measures the amount of drug (e.g., insulin) that is injected. The size and weight of such unit make it acceptable to carry the device attached to the pen in a pocket or purse, in the same way a user would carry a stand-alone pen. Preferably, the device does not impede normal functions of the drug delivery device, including turning the dosing dial, viewing the selected dose in the dose window, and pressing on the injection button to deliver a dose. After attaching the medical module, it does not add more steps to the process of using a drug delivery device during typical injections. The unit also records the amount of drug, such as, for example, insulin and date and time of the injection in memory, and may transmit the data to a data management unit for review by healthcare practitioners. In one preferred embodiment, the data management unit may include a paired analyte meter (e.g., a glucose meter which may be a non-continuous glucose meter or continuous glucose sensing meter) that receives or transmits data when the two devices are in range of each other. In such embodiment, the meter (not shown) keeps track of the drug dosing history, along with analyte (e.g., blood glucose values) for retrospective analysis by the patient and HCP. The device helps patients remember if they have taken their prescribed drug such as, for example, insulin, and may reduce the number of missed boluses, a key factor influencing HbA1c. The device also has several features that guide the user in the proper use of the drug delivery device, improving accuracy and reducing the burden of the HCP to train patients on insulin pen therapy. While the exemplary embodiments utilize a glucose sensory meter in the form of a data management unit, other types of analyte sensors may be used in conjunction with the module for the delivery of the appropriate injectable fluids such as, for example, growth hormone, GLP-1 analogs, Symlin, biologic molecules, and other injectable biopharmaceuticals.

First Type of Add-On Module

FIG. 1 illustrates a system that includes a medical device 224 and a medical module 202. The medical device can be a drug delivery device 224 and the medical module can be a communication module 202. The communication module 202 can be configured to monitor the activity of the drug delivery device 224. Add-on communication module 202 and drug delivery device 224 can both be configured to mate together as a single unit.

Drug delivery device 224, which may also be referred to as a drug delivery pen, can have a generally tubular pen housing that extends from a first end 212 and a second end 213, as shown in FIG. 1A1. Drug delivery device 224A is depicted in an initial state and drug delivery device 224B is depicted after a dosage setting was performed. The first end 212 of the housing can enclose a cartridge 222 that is configured to contain a drug such as, for example, insulin or other drugs. An end of cartridge 222 can be sealed by a piston 225 where movement of piston 225 causes the drug to be dispensed. The second end 213 of the pen housing can have a dosage selector 220 that is operatively coupled to piston 225. A pressing of pen button 216 (with the concomitant movement of dosage selector 220) can initiate the dispensing of the fluid using actuation unit 200. The dosage display 218 can output the amount of fluid dispensed on a display screen such as a printed display or a LCD, as illustrated in FIG. 1. The dosage selector 220 can control a user selected amount of drug or bio-effective fluid to be dispensed.

The actuation unit 200 can include a mechanism to dispense a controlled volume of fluid from cartridge 222. Referring to FIG. 1A1, actuation unit 200 can include a pen button 216, a dosage selector 220, an inner cylinder 23, a lead screw 25, a plunger rod 226, a plunger rod holder 27, and a first screw 35. The actuation unit 200 can include a mechanism (for brevity, shown as actuation shaft 190, plunger rod member 226) to dispense a controlled volume of fluid from cartridge 222. Rotation of dosage selector 220 in a clockwise or counterclockwise direction can cause dosage selector 220 to telescope outwards in a linear direction 1 or 2 (see FIG. 1C2). Dosage selector 220 can have a tubular portion that extends along an inner portion of the pen housing. An outer surface of the tubular portion can have a threaded assembly that is engaged to a first screw 35, which causes the telescoping motion of dosage selector 220. First screw 35 can be attached to an inner portion of the pen housing. Inner cylinder 23 can be concentrically assembled within an inner portion of dosage selector 220. Inner cylinder 23 can be coupled with a threaded assembly of lead screw 25. Note that inner cylinder 23 can also rotate with dosage selector 220 when setting a dosage amount. Pushing button 216 towards the first end 212 causes the dosage selector 220 to uncouple with inner cylinder 23 and move lead screw axially so that plunger rod 226 and piston 225 dispense insulin.

Figure 2:
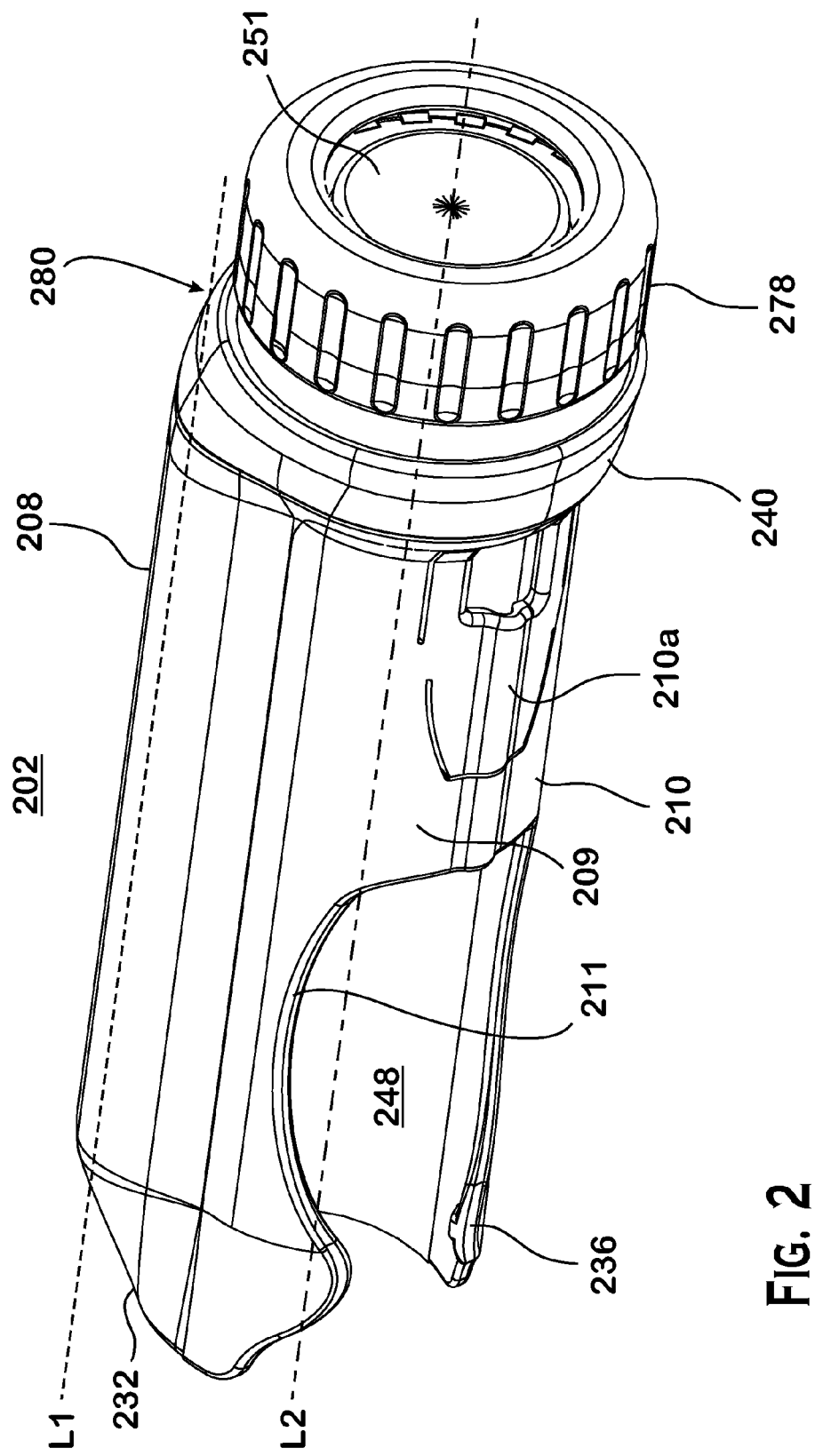
Figure 3:
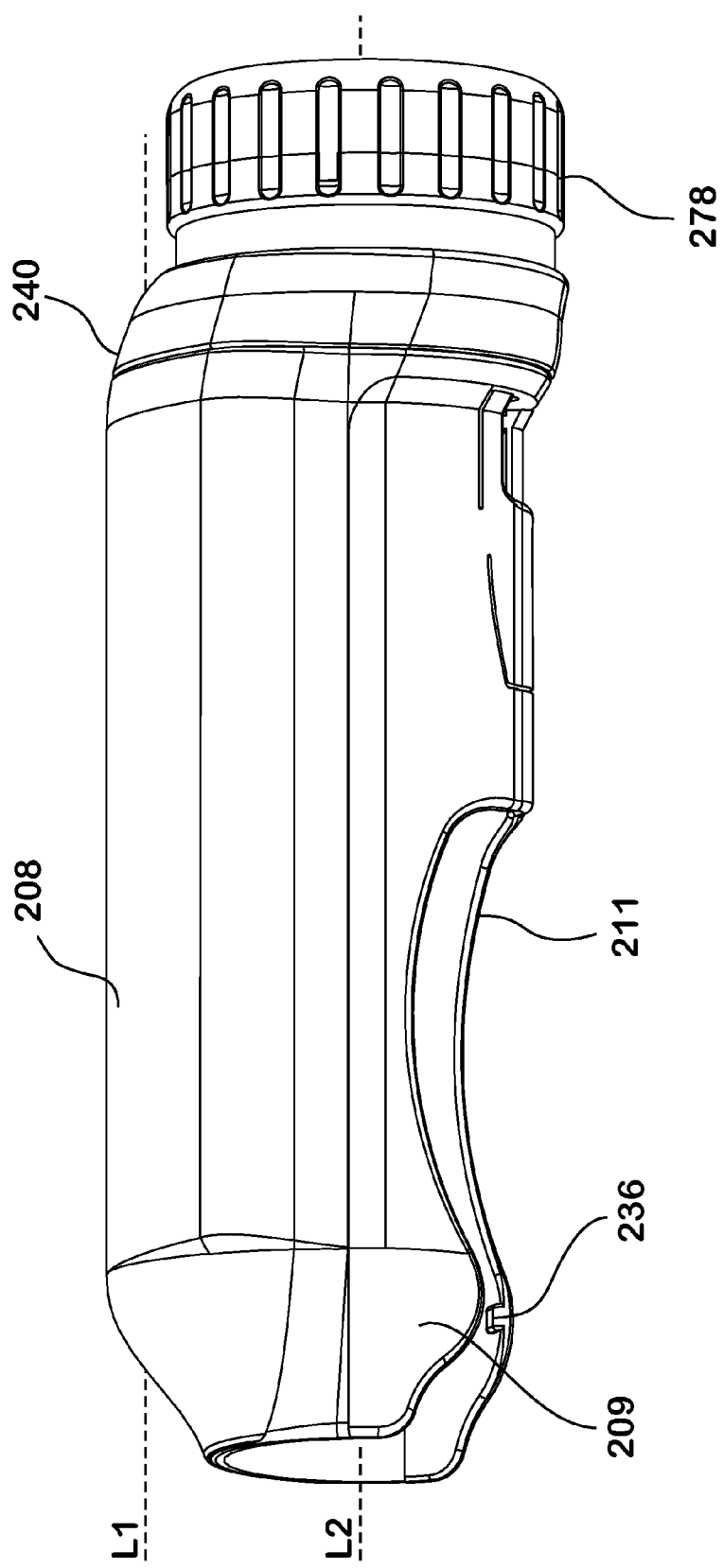
FIG. 3 illustrates a side perspective view of the first type of medical module, according to an exemplary embodiment described and illustrated herein.
Figure 4:
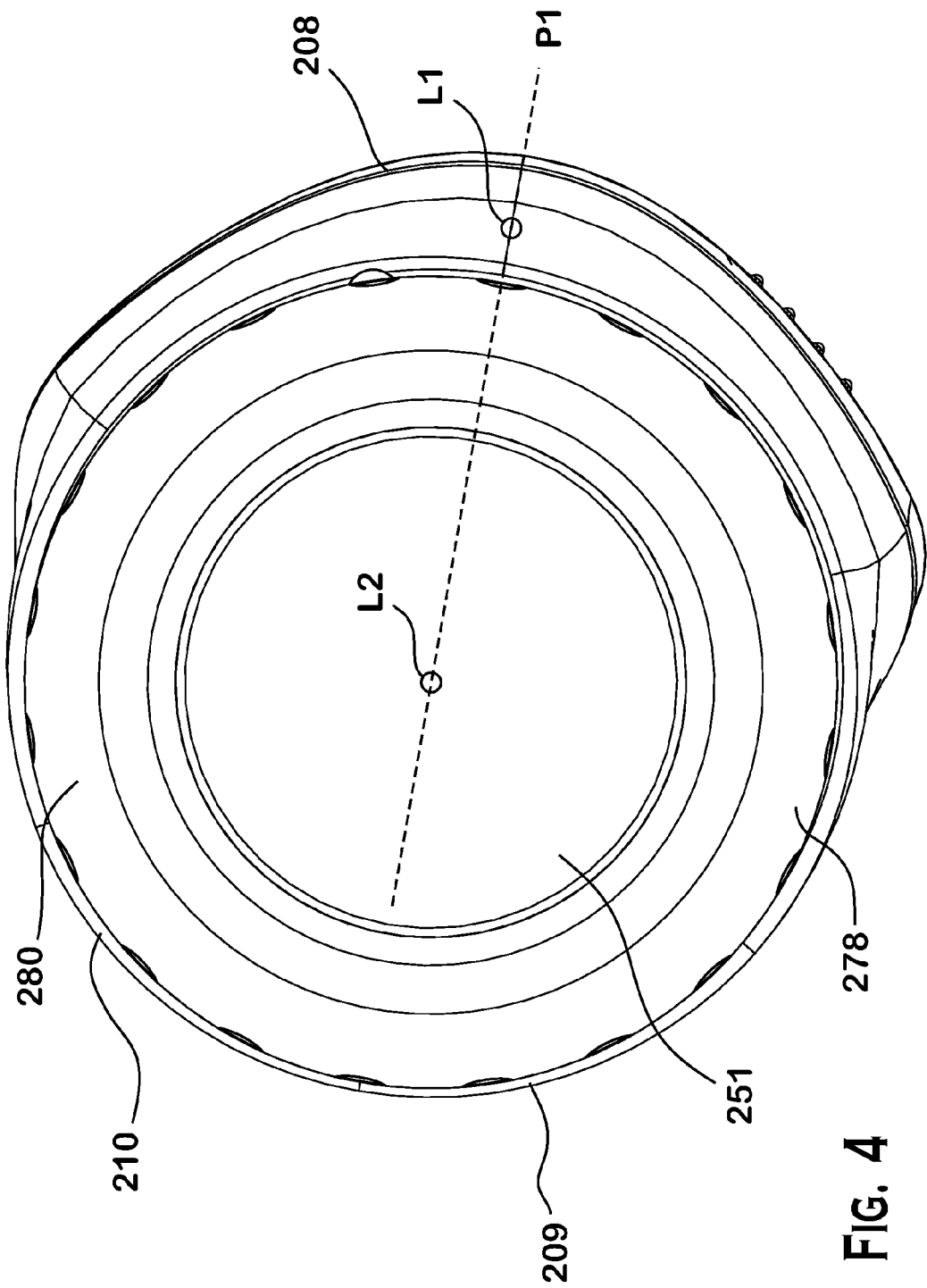
FIG. 4 illustrates a top view of the first type of medical module, according to an exemplary embodiment described and illustrated herein.
Figure 6:
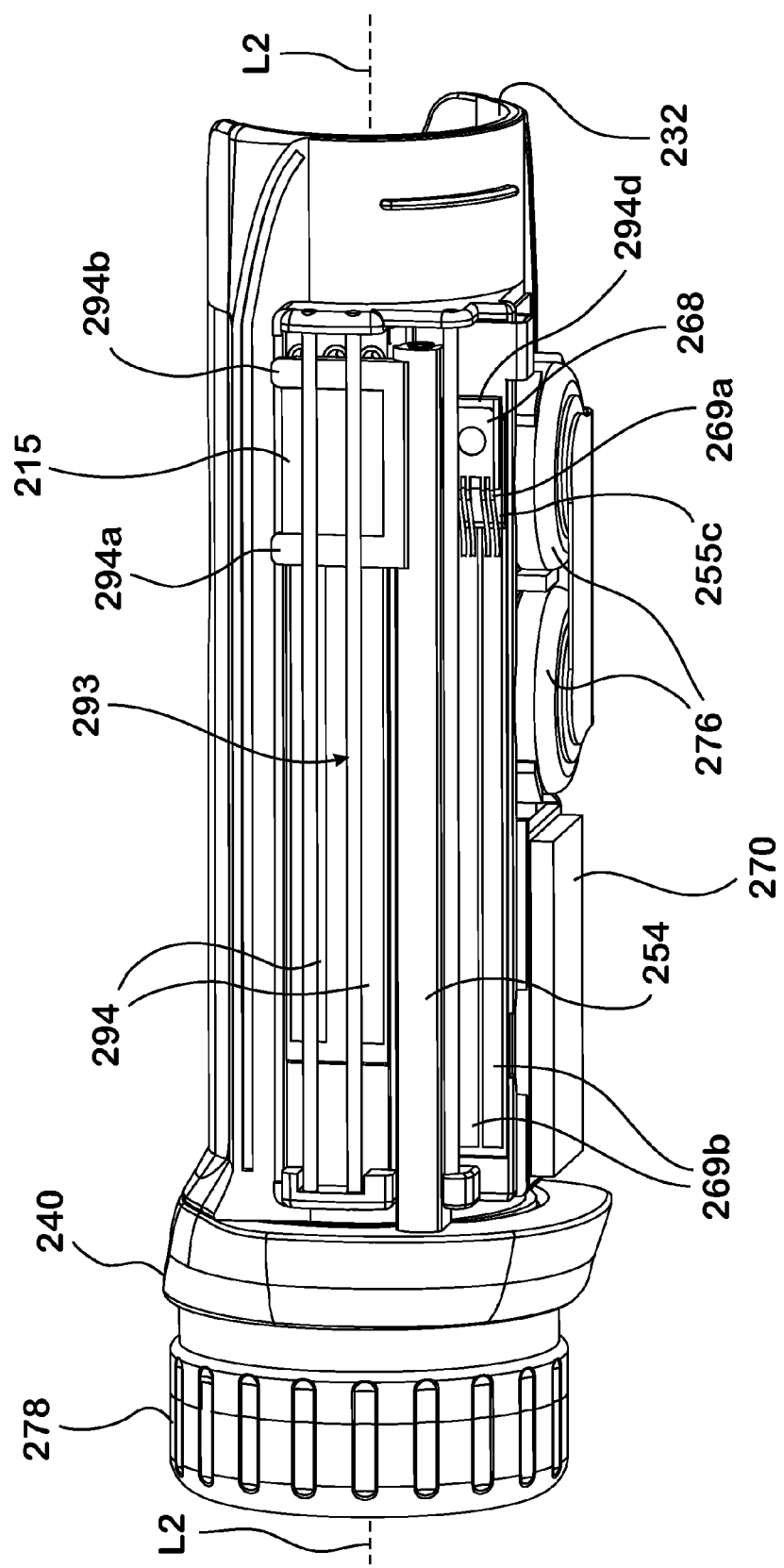
FIG. 6 illustrates a simplified back view of the first type of medical module with a cover removed to show internal components, according to an exemplary embodiment described and illustrated herein.

Add-on communication module 202 can have a first end 232 and second end 280. Add-on communication module 202 can include a primary module housing 208 and a secondary module housing 209, as illustrated in FIGS. 2 to 4. Together the primary module housing and the secondary module housing can form an add-on module housing that attaches to a drug delivery device. Secondary module housing 209 can have a generally cylindrical structure with an outer surface 210 and a hollow bore 248. A longitudinal axis L2 can extend along a center point of a circular portion of hollow bore 248, as illustrated in FIGS. 2 to 4. Primary module housing 208 can have a generally crescent shaped structure that partially circumscribes around an outer portion of secondary module housing 209. Primary module housing 208 can be in the form of a casing that includes three wall surfaces that together with the outer surface 210 of housing 209 provide for enclosure of certain components. Primary module housing 208 encloses a circuit board 270, sensor 214 (which includes a sensor slider 215), and power supply 276, which are disposed over an outer surface 210 of housing 209, as illustrated in FIGS. 2 and 6. Power supply 276 is accessible through power supply compartment door provided on casing 208. A longitudinal axis L2 can extend along an approximate mid-way point of a plane of symmetry P1, as illustrated in FIG. 4. The longitudinal axes L1 and L2 can be approximately parallel.

Electrical circuit components (not shown due to placement of components in the drawings) disposed on board 270 can include, a microprocessor, a microcontroller, an analog-to-digital converter, a speaker, a display, a memory, a display driver, a user interface driver, a transmitter, a receiver or a transmitter-receiver (e.g., a wireless transceiver using infrared light, radio-frequency, or optical waves), an inertial or acceleration sensor, and an antenna to send and receive wireless signals to and from the add-on module 202, process input from the sensor, turn the device on and off, put the device into sleep mode, wake the device up, regulate power from battery 276, and store and retrieve information to and from memory, as examples.

Dosage sensor 214 is preferably a linear potentiometer and is used to measure the position of dosage selector 220 for determining the size of the bolus injected by the user. Sensor 214 is electrically coupled to an analog-to-digital converter, which is coupled to microprocessor board 270 to provide data on the position of dosage selector 220 and dosage actuator 216. Other sensors that may be used with the exemplary embodiments include rotational potentiometers, linear, or rotational encoders. Linear potentiometers are preferred in the operational prototypes built by applicants. However, the embodiments described herein may utilize means for determining displacement of a dosage selector of a drug delivery pen in which the means include a follower, longitudinal member, and a dosage sensor (which may include rotary potentiometer, linear potentiometer, capacitive displacement sensor, optical displacement sensor, magnetic displacement sensor, encoder type displacement sensor, or combinations and equivalents thereof) and equivalents to these components described herein.

Casing 208 is located asymmetrically with respect to longitudinal axis L2 of secondary module housing 209 because casing 208 is disposed over outer surface 210 of housing 209. To further reduce the offset profile of casing 208, power supply 276 may be located proximate to knob 278 instead of inside casing 208. Power supply can be in the form of a disk shape similar to button 251 and disposed proximate to button 251 in a stacking relationship. As with the primary module housing and secondary module housing, the hollow bore is adapted to be coupled to a drug delivery pen in one operative mode and to be separated from the pen in another operative mode. In an embodiment, hollow bore 248 may have proximity detector 233 where the coupling or uncoupling of the drug delivery pen can be detected when it is mated, as illustrated in FIG. 1. Actuation of proximity detector 233 can be detected using the microprocessor. In another embodiment, the coupling or uncoupling of the drug delivery pen can be detected when it is mated by using an optical reader for detector 233 that is integrated with module 202. Further, the optical reader for detector 233 can be configured to recognize the type of insulin being coupled to module 202. Upon separation from the pen, the add-on module is no longer coupled to the actuation mechanism of the pen and in fact is lacking in an actuation mechanism, e.g., a plunger rod, push rod, or the like to dispense insulin, such that an internal surface of the hollow bore is exposed to the ambient environment so as to be visible to an ordinary observer or user.

Figure 1B:
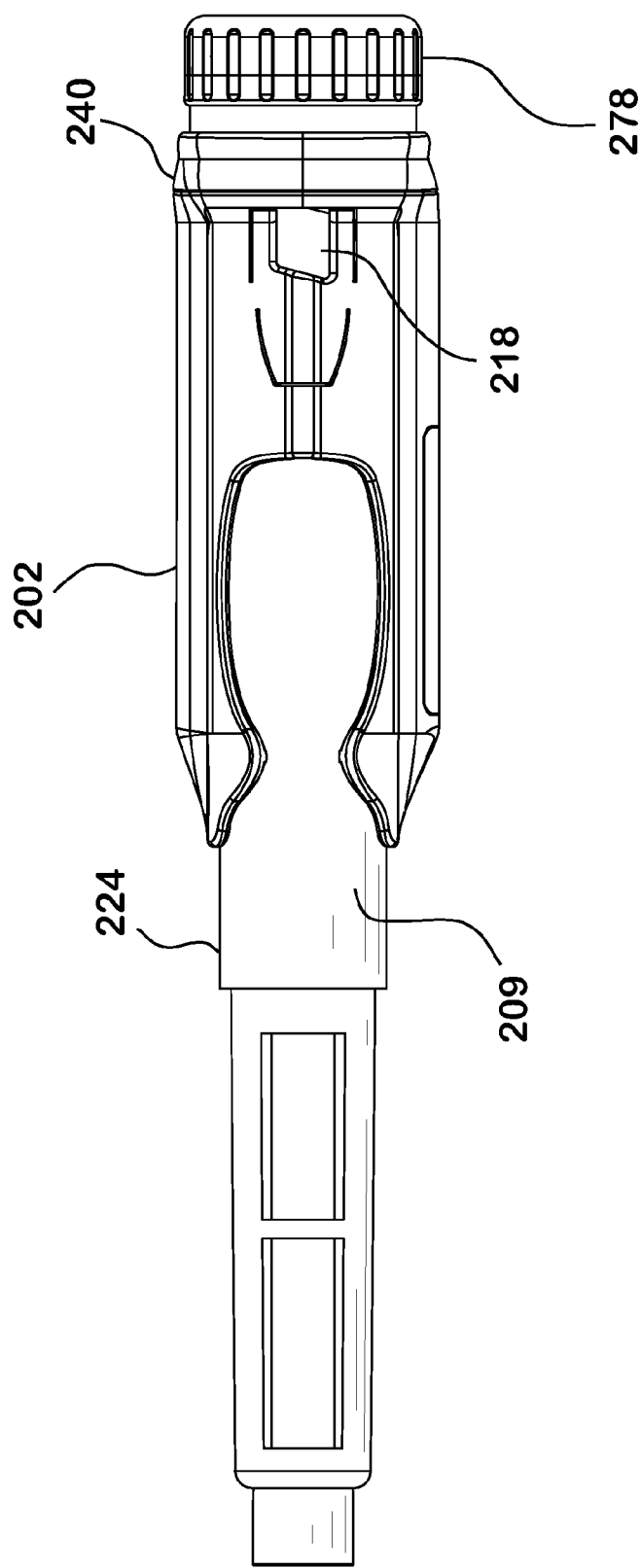
FIG. 1B illustrates a front view of a drug delivery pen and the first type of medical module, where the medical module has been attached to the drug delivery pen, according to an exemplary embodiment described and illustrated herein.

Housing 209 extends from a first end 232 to second end 280 along longitudinal axis L2 to define at least a portion of a hollow bore 248 formed from continuous surface 210 of housing 209, as illustrated in FIGS. 2 and 3. Continuous surface 210 is provided with a scallop portion 211 (FIGS. 2 and 3) that is distinct from other embodiments. While a housing 209 can be formed from a transparent or translucent material, such material can cause visual distortion of printed indicia on drug delivery pen 224. As such, scalloped opening 211 allows for printed identification on drug delivery device 224 to be visible to the user once unit 204 has been coupled to pen 224. Module 202 is coupled to drug delivery pen 224 by inserting bore 248 with scallop 211 closest to dosage selector 220 of pen 224 (FIGS. 1 and 1B). As module 202 is inserted onto pen 224, a groove 210a on module 204 (FIGS. 1 and 1B) is aligned with a raised ridge 210b on pen 224 to fix module 202 rotationally with respect to pen 224. In addition, a tang 236 may be used to engage to a recess in pen 224.

Add-on module 202 can be configured to monitor the amount of insulin dialed in by the user and also the time in which the user injected the insulin. A user can rotate dosage selector 220 in a clockwise or counter clockwise manner that causes dosage selector 220 and pen button 216 to telescope outwards 1 or inwards 2 (FIGS. 1C1 and 1C2). Drug delivery pen 224a shows an example where no dosage amount has been dialed in with dosage selector 220. In contrast, drug delivery pen 224b shows an example where dosage selector has been rotated such that a predetermined amount of insulin has been set. The user can then depress pen button 216 causing dosage selector to move inwards, which in turn causes a plunger to dispense insulin. In an embodiment, communication module 202 can monitor both the inward and outward movement of dosage selector 220 for monitoring the activity of the drug delivery pen.

Figure 5:
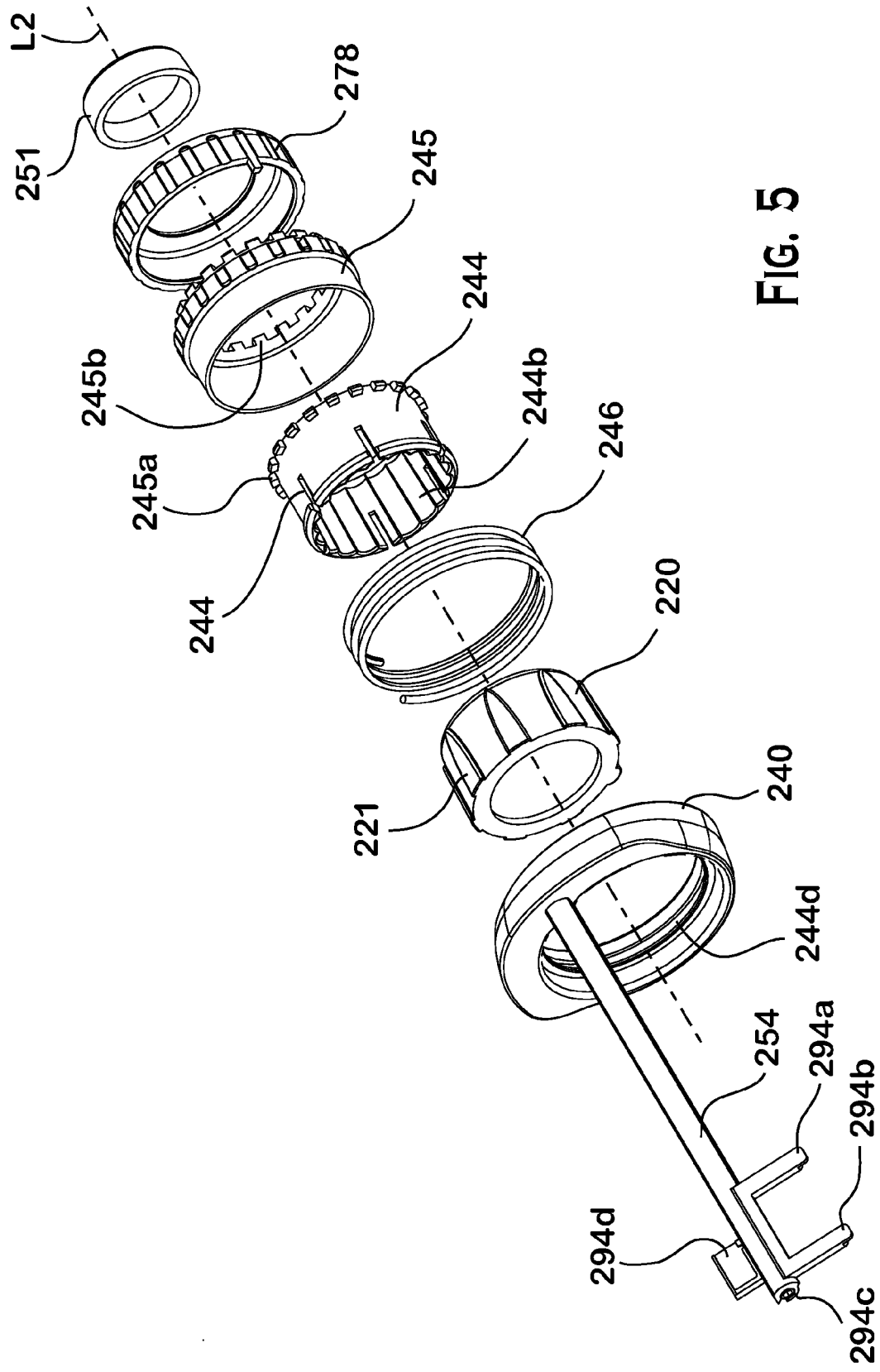
FIG. 5 illustrates a simplified perspective view of a mechanism for coupling the movement of the dosage selector cap with a follower and a rotating knob, according to an exemplary embodiment described and illustrated herein.

The following will describe a mechanism for monitoring the activity of a drug delivery device by coupling the movement of the dosage selector cap to a follower portion 240 contained within communication module 202. A linear movement of the follower portion can then be measured with a sensor. FIG. 5 illustrates a simplified perspective view of the mechanism for coupling the movement of dosage selector cap 220. Note that for simplicity only the dosage selector cap 220 of drug delivery device 224 is depicted in FIG. 5.

Coupled to housing 209 are a follower portion 240, and rotatable knob 278, as illustrated in FIGS. 1B, 2, and 3. Both of follower portion 240 and knob 278 are preferably continuous through-bores that are in alignment with bore 248 (see FIGS. 2, 3, and 5). Bore 248 is configured to allow actuation unit 200 of drug delivery pen 224 to be slipped into bore 248 until actuation pen button 216 abuts with a button 251 of module 202 (see FIGS. 1, 1B, and 2). In the preferred embodiment of FIGS. 2 and 5, bore 248 is a through bore which is contiguous with bore of rotatable knob 278 and continuous surface 210 of housing 209 and defines a generally tubular member. As noted earlier, secondary housing 209 is preferably formed from a substantially transparent or translucent material while casing 208 may be formed with any suitable color or combination of colors. As used herein, the actuation unit 200 of a drug delivery pen is that portion of the pen on which at least the dosage selector, actuator and actuation button are provided for attachment to a drug cartridge 222.

As shown in FIG. 5, follower 240 is coupled to capture ring 244 via a retention system having a groove 244d on follower member 240 and a corresponding ridge 244c on capture ring 244. Follower 240 and capture ring 244 can be coupled together such that capture ring 244 is rotatable around second longitudinal axis L2 and that follower 240 does not rotate, but moves in a linear manner parallel to second longitudinal axis L2.

Capture ring 244 may include longitudinal slits 244a that extend along longitudinal axis L2 to provide flexibility in the magnitude of the diameter of capture ring 244, which allows inner undulating surfaces 244b of capture ring 244 to frictionally couple to raised ribs 221 of dosage selector 220 (of pen 224). Inner undulating surfaces 244b may be configured to allow for a taper converging towards axis L2 to ensure little or no interference when ribs 221 first engage undulation 244b yet with frictional engagement upon full insertion of module 204 into pen 224. Capture ring 244 may be provided with external splines or teeth 245a that are in engagement with internal splines or teeth 245b of a coupling ring 245. Coupling ring 245 can couple together rotatable knob 278 and capture ring 244. The mechanical assembly of capture ring 244, coupling ring 245, and rotatable knob 278 causes dosage selector 220 to rotate as a result of a rotation of rotating knob 278 when the dosage selector 220 is frictionally engaged.

Actuation button 251 is also coupled to knob 278 so that button 251 of module 202 is in contact with pen button 216 once both components are assembled together. A spring 246 can be located on an outer surface of capture ring 244 and an inner surface of knob 278. Spring 246 can be configured to bias coupling ring 245 against capture ring 244 such that when teeth 245a are engaged, turning knob 278 causes dosage selector 220 to turn. During an injection, pressing button 251 can compress spring 246, allowing coupling ring 245 to disengage from capture ring 244. It should be noted that rotatable knob 278 disengages from capture ring 244 during actual injection so that the knob does not rotate under the user's thumb while drug is being delivered, i.e., during the injection. After injecting, teeth 245a re-engage with teeth 245b, allowing the user to dial in a new dosage on the pen. Knob 278, however, may need to be rotated slightly before the teeth re-engage if they are not properly lined up after the injection.

Follower 240 can include a longitudinal member 254, as illustrated in FIG. 5. Longitudinal member can have a tubular structure where one end is coupled to a ring portion of the follower 240. A hollow portion 294c of the tubular structure is depicted in FIG. 5. The other end of longitudinal member can have a protrusion plate 294d and two slider fingers 294a and 294b.

Referring to FIG. 6, longitudinal member 254 may be configured to slide axially along axis L2. Follower portion 240 is constrained to move with knob 278 as knob 278 is moved axially by rotating knob 278 about axis L2. As knob 278 is rotated, capture ring 244 is constrained to also rotate, which causes the rotational motion of capture ring 244 to be transferred to dosage selector 220. Since any rotary motion of selector 220 will result in inward or outward axial movement along axis L2, capture ring 244, follower 240, and knob 278 are constrained to move in the same manner as dosage selector 220 (axially for follower 240, and both axially and rotationally for capture ring 244 and knob 278). Hence, movements of the dosage selector 220 are determined via a dosage sensor as proportional to a dosage quantity to be delivered or injected. In the preferred embodiments, the dosage sensor, which provides dosage amount information, is a potentiometer. In the embodiment of FIGS. 1C1 and 1C2, the drug delivery pen may be a Lantus SoloStar manufactured by Sanofi Aventis.

FIG. 6 illustrates a simplified back view of certain components contained within primary module housing 208 where some of the walls were removed. To reduce the profile of module 202, applicants have utilized a sliding potentiometer configuration, as illustrated in FIG. 6. Module 202 also utilizes a slider 215 on potentiometer tracks 294, where slider 215 is coupled in between both slider fingers 294a and 294b. Conductive contacts (not shown) can be disposed on a surface of slider 215 to allow an electronic circuit to determine the position of the slider on the potentiometric tracks 294. The tracks 294 may be conductive polymer tracks or ceremet tracks or alternatively tracks formed from carbon, gold or a mixture thereof. Hollow portion 294c (see FIG. 5) of longitudinal member 254 can be configured to couple to an activation shaft 297 (see FIG. 7) to ensure that the slider is constrained for translation along axis L1 and also for switching a micro switch 268.

Figure 7:
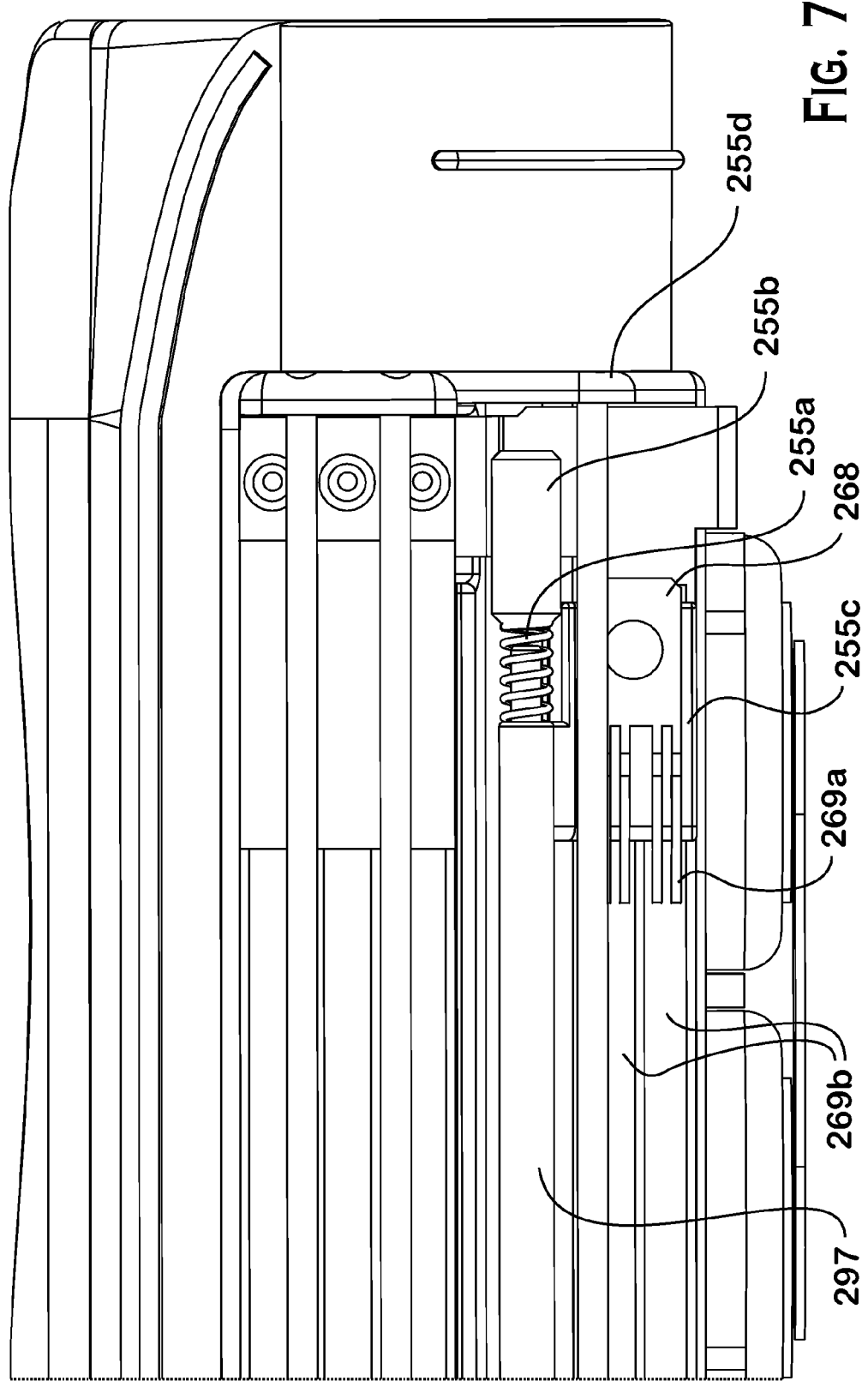
FIG. 7 illustrates a close-up back view of FIG. 6 with the follower removed to show internal components, according to an exemplary embodiment described and illustrated herein.

Referring to FIG. 7, longitudinal member 254 is removed to show activation shaft 297 that was disposed inside longitudinal member 254. Activation shaft 297 is connected to a separator member 255c, which interacts with fingers 269a of micro switch 268. Hollow portion 294c and protrusion plate 294d can be keyed to correspond to separator member 255c so that separator member moves along axis L1 when button 251 is depressed. Activation shaft 297 may be coupled with a spring 255a and a setscrew 255b for adjustment of the position of separator 255c with respect to fingers 269a of micro switch 268. Because fingers 269a are normally out of contact with conductive tracks 269b, switch 268 is normally-open whenever button 251 is not depressed fully (e.g., during a dosage selection or adjustment). Upon button 251 being fully depressed, such as during a dosage injection, longitudinal member 254, activation shaft 297, and separator 255c are constrained to move along longitudinal axis L1 until setscrew 255b abuts against retainer wall 255d. As setscrew 255b approaches retainer wall 255d, separator 255c lowers fingers 269a of micro switch 268 onto conductive tracks 269b, creating a closed circuit. Further movement of dosage button 251 causes hollow longitudinal member 254 to continue axially to take up any slack provided between an end of a rod portion of activation shaft and setscrew 255b.

By virtue of the configurations described exemplarily herein, applicants have now been able to provide the means for determining the difference between either or both of a dosage delivery event and duration of such dosage delivery or injection event. Specifically, where a user is merely rotating knob 278 to thereby move knob 278 longitudinally along axis L2 in either direction to select dosages, there is no contact of fingers 269a of switch 268 and hence no determination that a dosage event is taking place. Except for a determination that a dosage selection is being made, no recording is made in the memory of processor board 270 regarding a dosage delivery. Only upon the full depression of button 251 would there be contact of fingers 269a with tracks 269b, (FIGS. 6 and 7) triggering a determination that dosage delivery is taking place. In an embodiment, the electronics can be configured to go into "sleep" mode, until button 251 is depressed, which reduces the power consumption of the module. As used herein, the "sleep" mode is one in which all functionalities of the module are at minimal or virtually zero power consumption but which does not require a system boot up in the event that the pen is taken out of sleep mode.

It should be noted that the micro-switch 268 also enables tracking of the injection start point and the injection end point, so the volume of the injection can be calculated, even if the user does not press the injector button all the way to the zero dosage position. While the ability to determine when a dosage delivery has been made is valuable to a user in managing diabetes, applicants believe that it is the ability to determine and confirm the duration of such dosage delivery for later analysis with a compliance regiment that is a step forward in the art of diabetes management. That is, where a patient is injecting insulin per a protocol as prescribed by a health care provider, such patient may not be in full compliance if the patient fails to deliver a complete prescribed dosage, which typically requires fully depressing button 251 for four (4) to ten (10) seconds. By recording the dosage, time and duration in memory of processor board 270 for transfer to a health care provider's computer, the health care provider is able to take steps, after review of data or even in real-time, to ensure that full compliance of the prescribed protocol is followed. In the preferred embodiments, a warning or reminder to the patient on proper pen usage technique can be displayed as a message on the data management unit, which in one embodiment includes a glucose meter. Thus, the means for determining one or more of dosage delivery or duration of dosage delivery of a drug delivery pen include, follower 240, longitudinal member 254, spring 255a, separator 269a, switch 268, a processor coupled to switch 268, in which processor is programmed to operate in the manner described herein, and equivalents to these components.

Second Type Of Add-On Module

Figure 8:
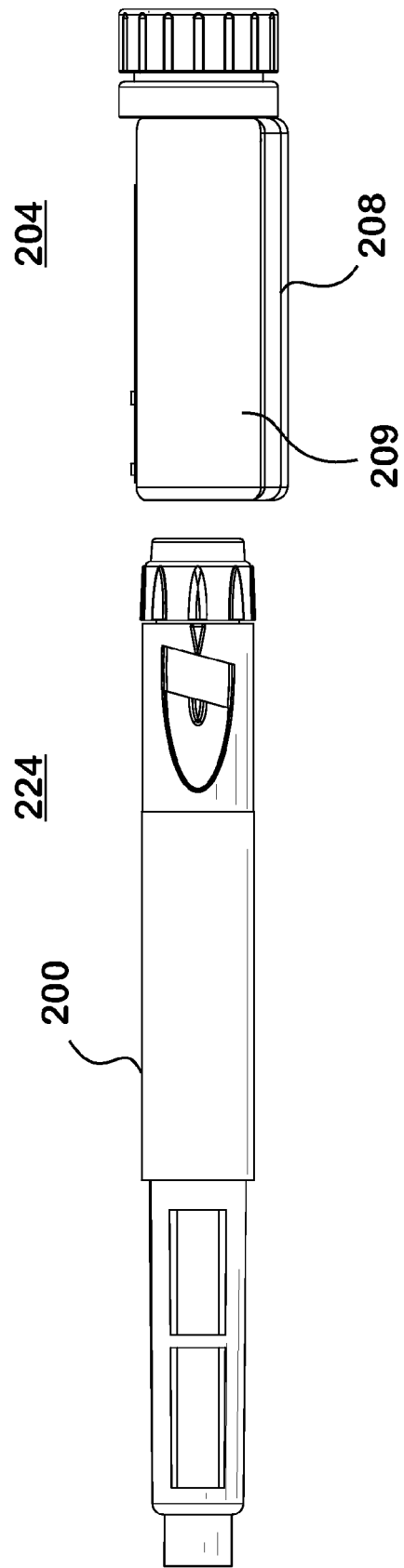
FIG. 8 illustrates a front view of a system that includes a drug delivery pen and a second type of medical module, according to an exemplary embodiment described and illustrated herein.
Figure 9:
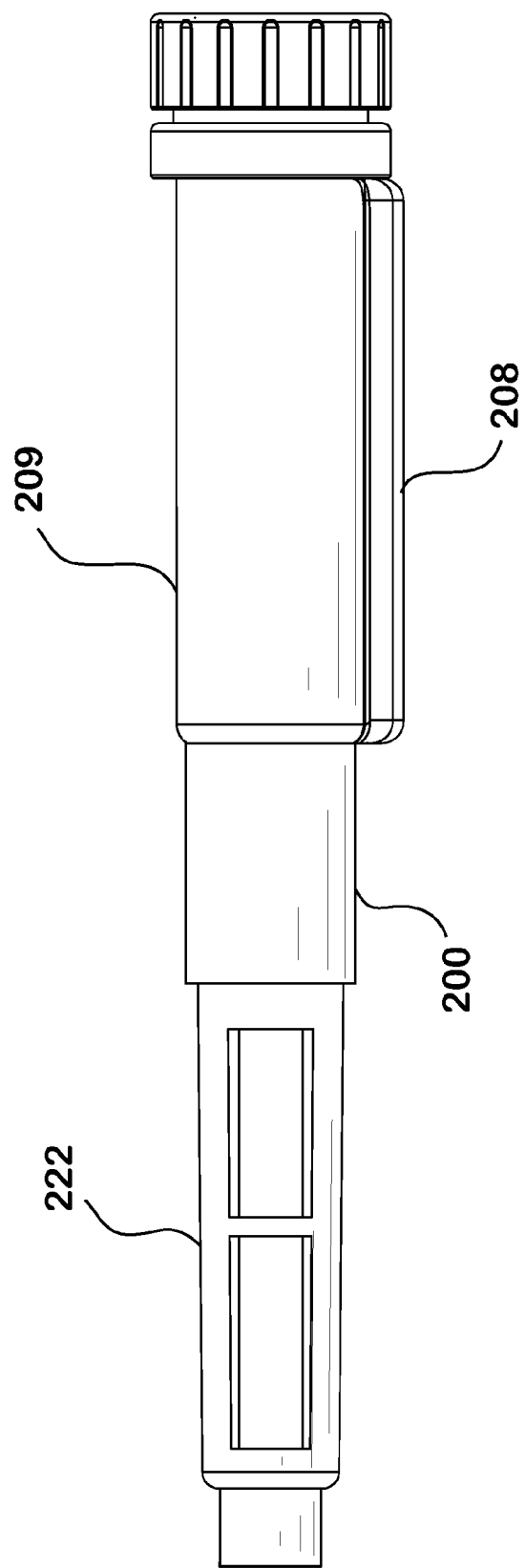
FIG. 9 illustrates a front view of a drug delivery pen and the second type of medical module, where the medical module has been attached to the drug delivery pen, according to an exemplary embodiment described and illustrated herein.

Recognizing that different drug delivery devices (e.g., insulin pens) may be required based on user preferences, applicants have provided for an alternative type of communication module 204, as illustrated in FIGS. 8 and 9. Add-on module 204 is similar to communication module 202 in that it can mate with drug delivery device 224 and monitor the activity of drug delivery device 224. However, communication module 204 does not have a scallop portion. Instead, communication module 204 has a secondary module housing 209 that is partially or fully made of a translucent material. The use of a translucent or transparent material will allow a user to read of a dosage display and printed identification on drug delivery device 224. Under certain circumstances, communication module 204 may provide for a more robust structure that is more resistant to irreversible distortions, and also bind more securely to the pen.

Third Type Of Medical Add-On Module

Figure 10:
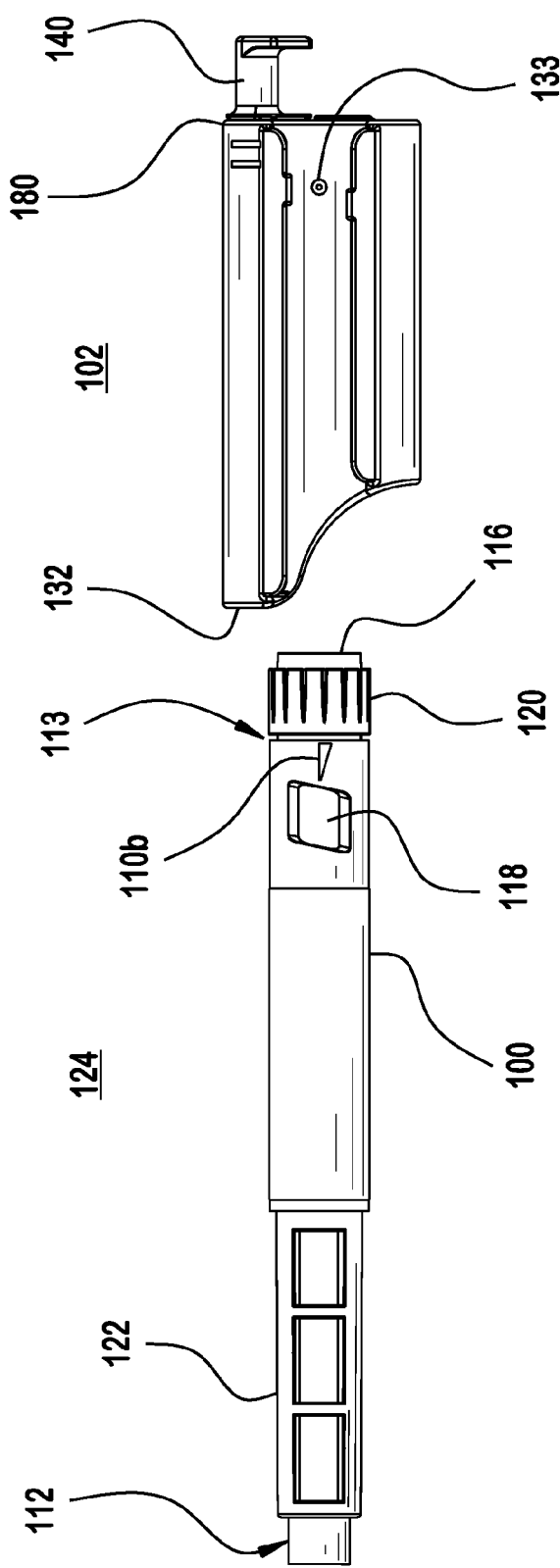
FIG. 10 illustrates a front view of a system that includes a drug delivery pen and a third type of medical module, according to an exemplary embodiment described and illustrated herein.

Recognizing that different drug delivery devices (e.g., insulin pens) may require alternative coupling techniques, applicants have provided for an alternative that is designed to be attached from the side rather than being inserted over one end of the drug delivery device, as in the prior embodiments. FIG. 10 illustrates a system that includes a drug delivery pen 124 and a medical module 102. Add-on module 102 and drug delivery pen 124 can be mated together, as illustrated in FIGS. 10, 11, and 11B.

Drug delivery pen 124 can have a first end 112 and a second end 113, as illustrated in FIG. 10. Note that drug delivery pens 124 and 224 can be similar in function for helping a user inject a controlled amount of insulin. At proximate first end 112, drug delivery pen can include a cartridge 122 that is configured to contain a drug such as insulin. At about the second end 113, drug delivery pen can include an actuation unit 100, a pen button 116, a dosage display 118, and a dosage selector 120. In the embodiment of FIG. 10, the drug delivery pen may be a NovoLog® Flex-Pen manufactured by Novo Nordisk.

Figure 12:
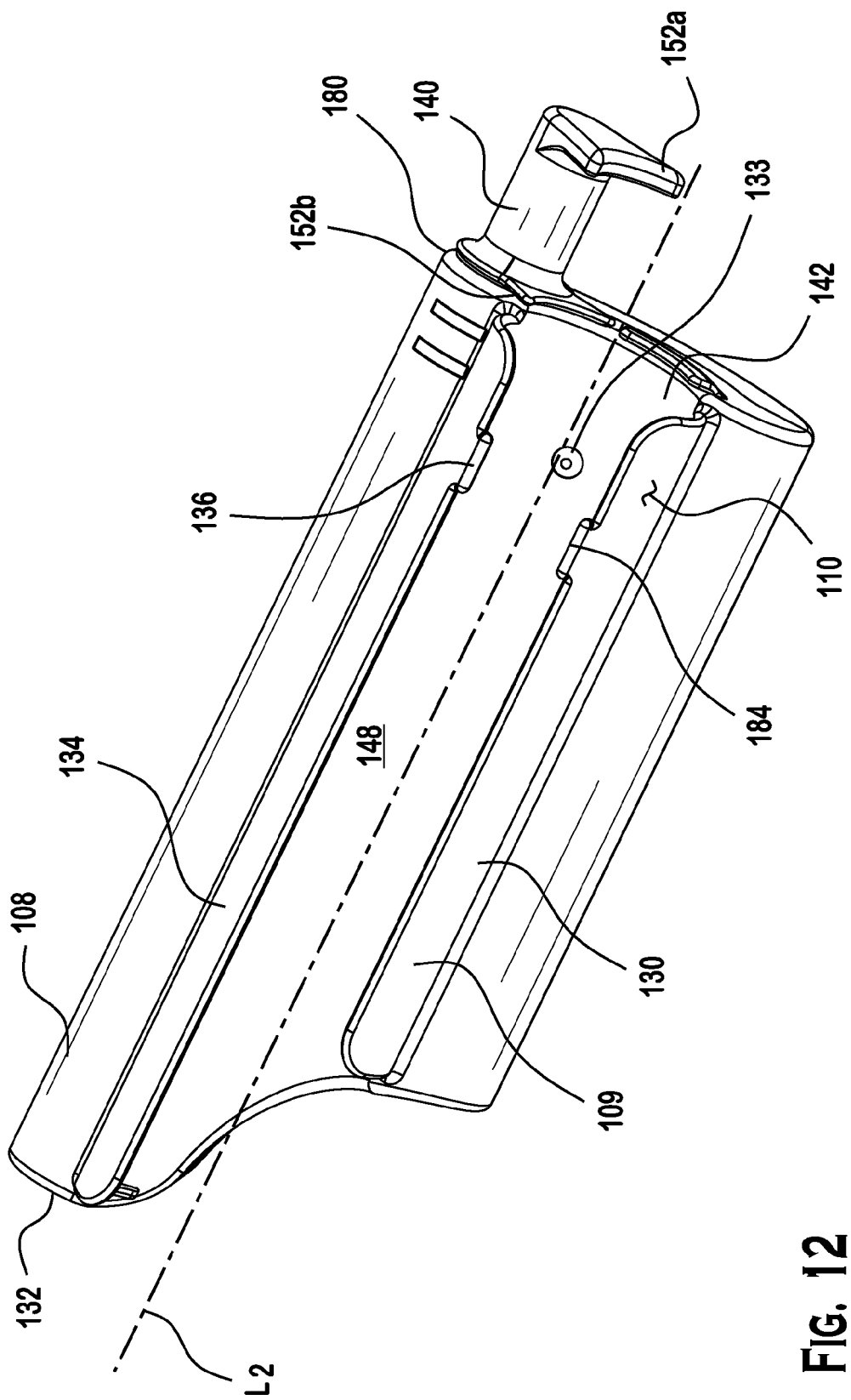
FIG. 12 illustrates a front perspective view of the third type of medical module, according to an exemplary embodiment described and illustrated herein.
Figure 13:
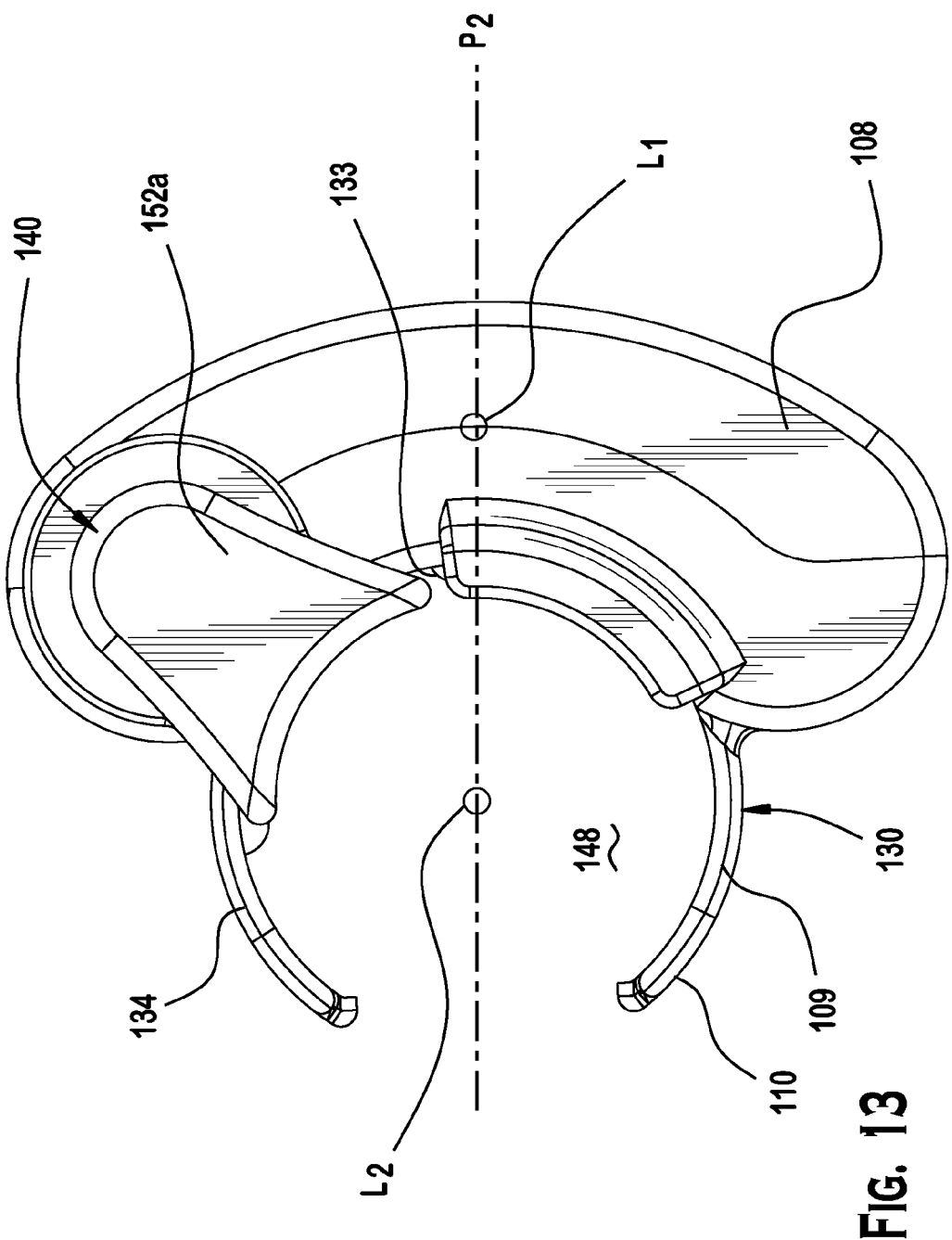
FIG. 13 illustrates a top view of the third type of medical module, according to an exemplary embodiment described and illustrated herein.

Add-on module 102 can have a first end 132 and second end 180. Add-on module 102 can include a primary module housing 108 and a secondary module housing 109, as illustrated in FIGS. 12 and 13. Secondary module housing 109 can have a generally cylindrical structure with an outer surface 110 and a hollow bore 148 (FIG. 13). Secondary module housing 109 can include first and second extension portions 130 and 134 that circumscribe about second axis L2 to define at least a portion of hollow bore 148. A longitudinal axis L2 can extend along a center point of a circular portion of hollow bore 148, as illustrated in FIGS. 12 and 13. In one embodiment, each of extensions 130 and 134 extends in a generally circular path about axis L2 of about 30 degrees. Where greater security of engagement between the extensions and the pen is needed, each of extensions 130 and 130 may be increased to define any ranges from generally 30 degrees to generally 250 degrees (or even 360 degrees to provide for a continuous bore as illustrated in FIG. 8) about axis L2.

Primary module housing 208 can have a generally kidney shaped cross-sectional structure (FIG. 13) that partially circumscribes around an outer portion of secondary module housing 109. A longitudinal axis L2 can extend along an approximate mid-way point of a plane of symmetry P2, as illustrated in FIG. 13. The longitudinal axis' L1 and L2 can be generally parallel.

Primary module housing 108 is preferably located asymmetrically with respect to longitudinal axis L2 of secondary module housing 109 because housing 108 is disposed over outer surface 110 of housing 109. As with the primary module housing and secondary module housing, the hollow bore 148 is adapted to be coupled to a drug delivery pen in one operative mode and to be separated from the pen in another operative mode. In one embodiment, shown here in FIG. 10, hollow bore 148 may have proximity detector 133 (e.g., switch, ultrasound, infrared or visible light detector) where the coupling or uncoupling of the drug delivery pen can be detected when the add-on module 102 is mated to the pen 224. Actuation of proximity detector 133 can be detected using a microprocessor of the add-on module 102. In another embodiment, the coupling or uncoupling of the drug delivery pen can be detected when it is mated by using an optical reader for detector 133 that is integrated with module 102. Further, the optical reader for detector 133 can be configured to recognize the type of insulin being coupled to module 102. Upon separation from the pen, the add-on module is no longer coupled to the actuation mechanism of the pen and in fact is lacking in an actuation mechanism, e.g., a plunger, push rod, or the like to dispense insulin, such that an internal surface of the hollow bore is exposed to the ambient environment so as to be visible to an ordinary observer or user.

Figure 14:
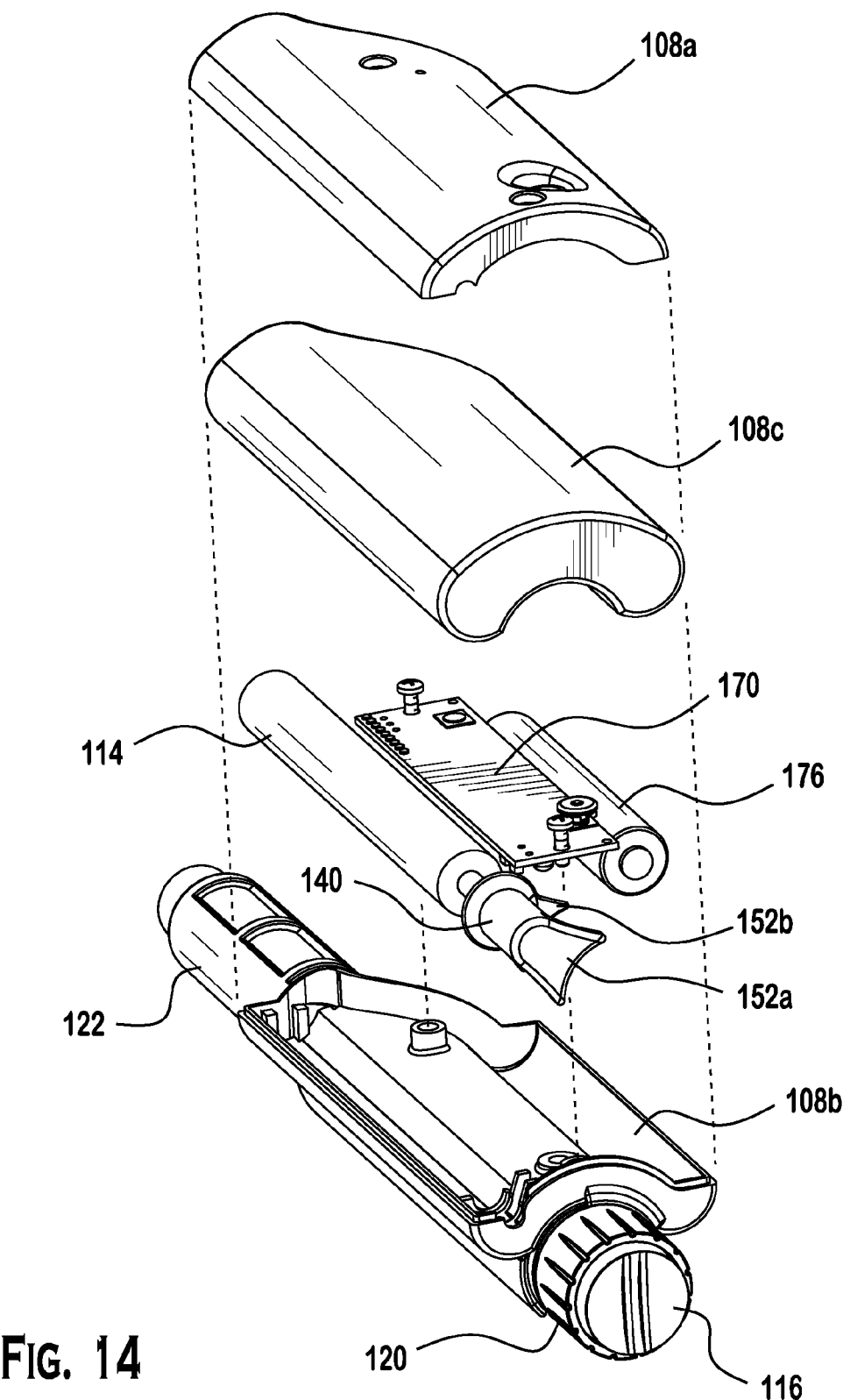
FIG. 14 illustrates an exploded perspective view of a primary housing module of the third type of medical module, according to an exemplary embodiment described and illustrated herein.
Figure 15:
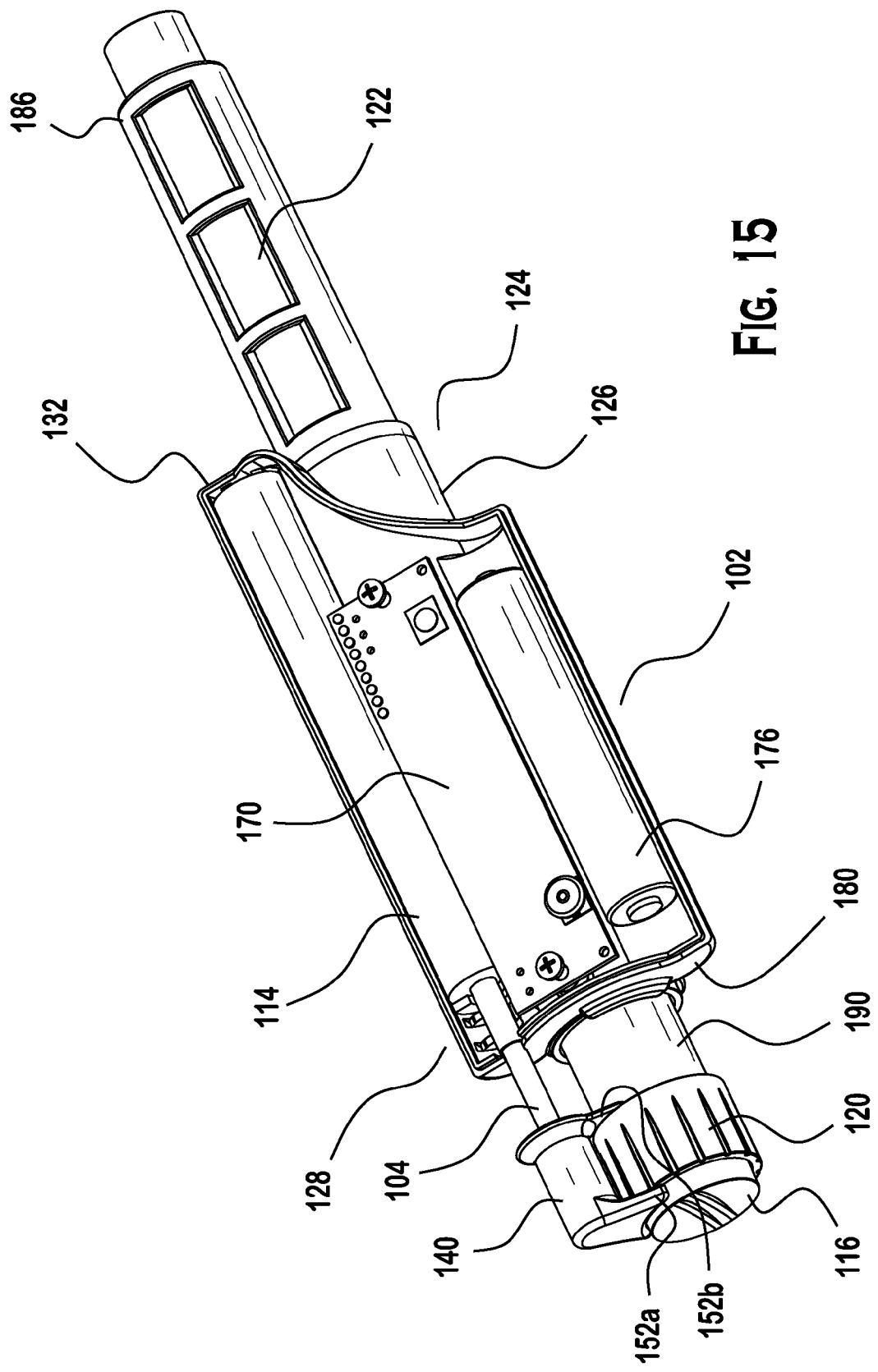
FIG. 15 illustrates a rear perspective view of FIG. 11A, where the rear cover of the medical module has been removed, according to an exemplary embodiment described and illustrated herein.

FIG. 12 illustrates primary module housing 108 that includes locator tangs 136 and 184 (which are offset longitudinal with respect to each other along axis L2), locator forks 152a and 152b with follower portion 140 that may reciprocate longitudinally along a longitudinal axis L1. Referring to FIGS. 14 and 15, follower portion 140 is configured to be physically connected directly to sensor 114 and permitted to rotate about its own axis. A power source 176 is also provided in a location preferably spaced apart from dosage sensor 114 (FIG. 14). A microcontroller, depicted here as a controller board 170 in FIG. 14, is coupled to both sensor 114 and power source 176 to allow for a determination of position, movements or even direction of movement of a dosage selector 120 (see FIGS. 14 and 15).

Figure 11A:
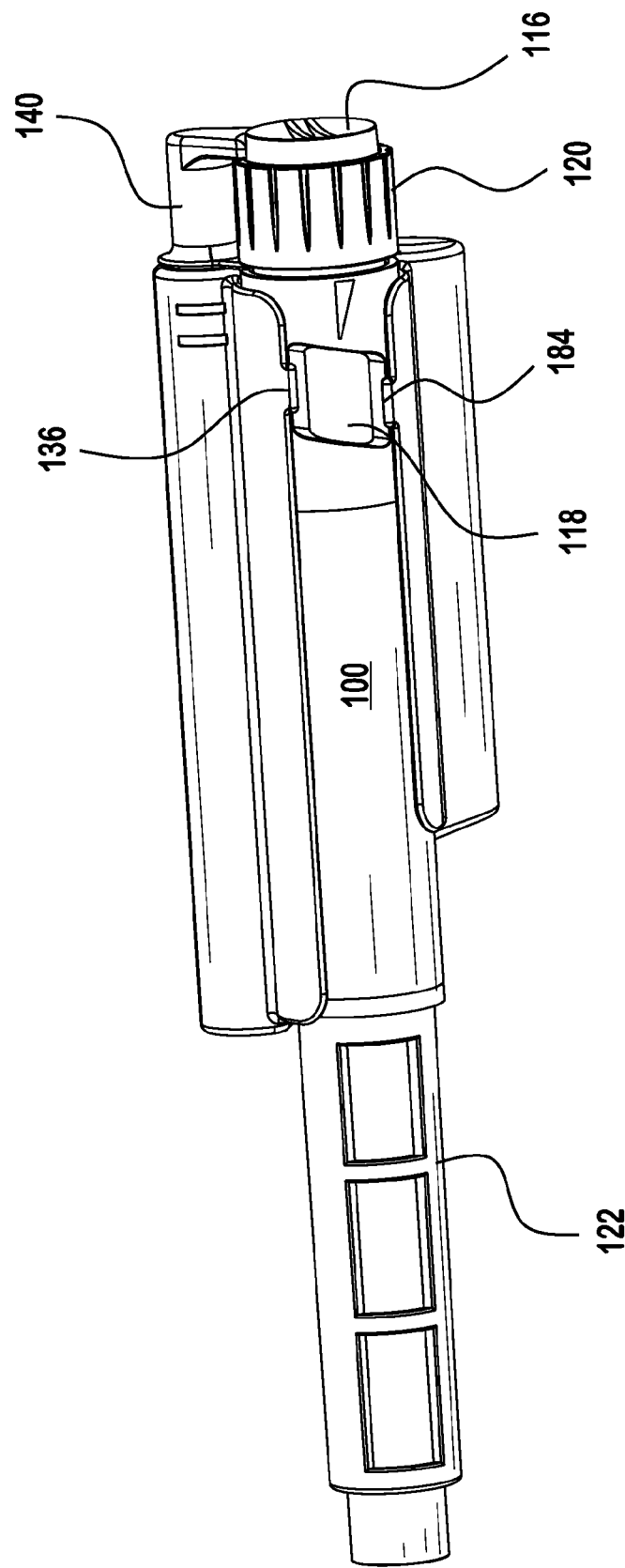
FIG. 11A illustrates a front perspective view of a drug delivery pen and the third type of medical module, where the medical module has been attached to the drug delivery pen, according to an exemplary embodiment described and illustrated herein.
Figure 11B:
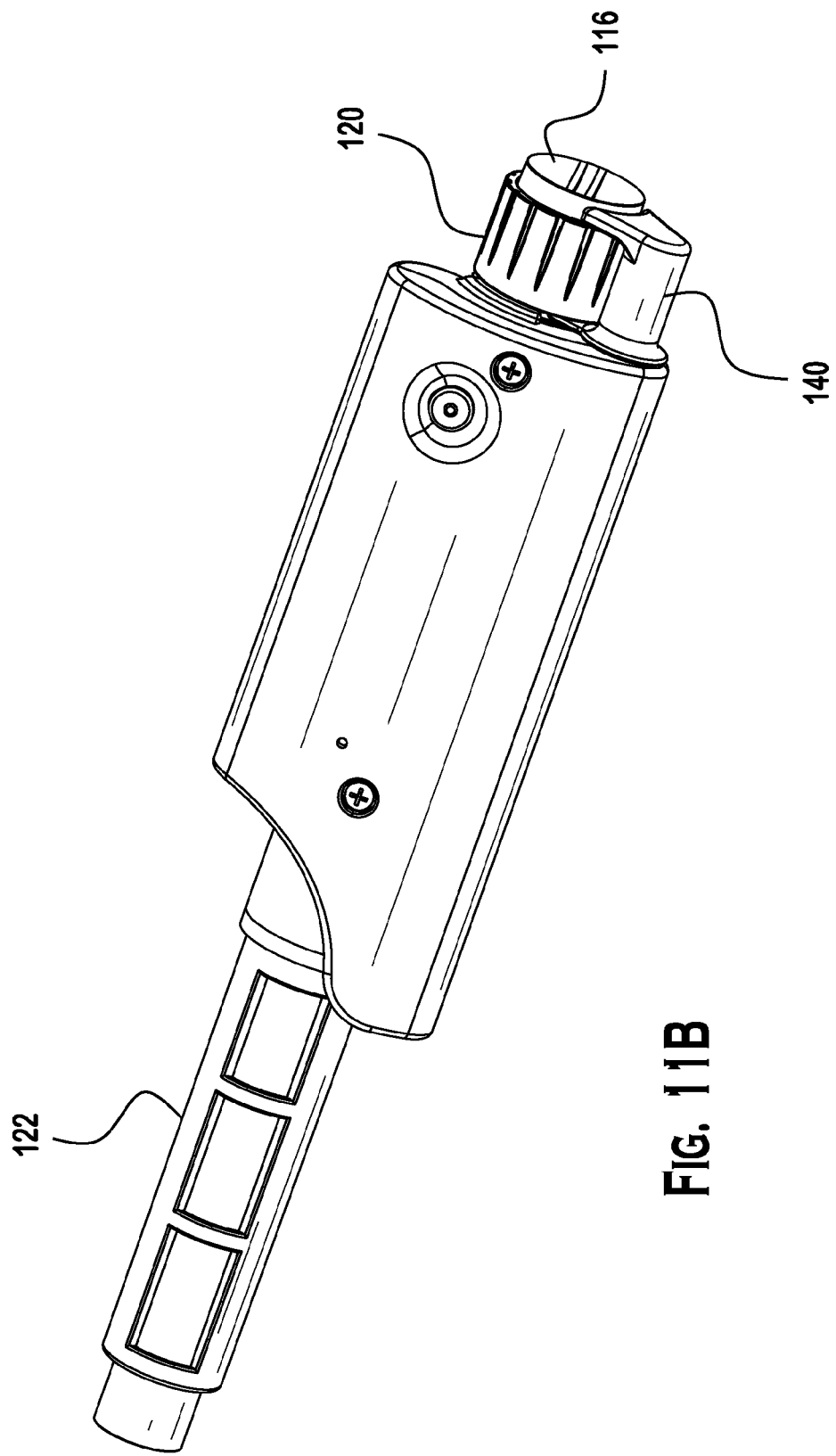
FIG. 11B illustrates a back perspective view of the drug delivery pen and the third type of medical module, where the medical module has been attached to the drug delivery pen, according to an exemplary embodiment described and illustrated herein.

FIG. 11A shows locator tabs 136 and 184 for aligning communication module 102 with dosage display window 118 of the pen. Locator tabs 136 and 184 align snap-on unit 102 with drug delivery device 124 and prevent unit 102 from rotating and obscuring dosage display window 118 of drug delivery device 124. For module 102, extensions 134 and 182, with locating tangs 136 and 184, allow communication module 102 to snap on over pen 124. After inserting drug delivery pen 124, locating tangs 136 and 184 engage dosage indicator window 118, and can secure medical module 102 to drug delivery pen 124. Dosage selector 120 engages follower portion 140, allowing dosage selector 120 to move along its axis as dosage is adjusted, as illustrated in FIG. 15. Extensions 134 and 182 leave an opening through which the user may view dosage indicator window 118 and labeling on the drug delivery pen 124. As shown in FIG. 15, locator forks 152a and 152b are coupled to dosage selector 120 such that follower portion 140 follows the axial movement of dosage selector 120 (which itself is rotational to allow for axial motion of dosage selector) or delivery button 116 (which is axial).

FIG. 14 shows an exploded perspective view of communication module 102 with the top housing removed to reveal the internal components. FIG. 15 shows the location of a longitudinal member 154 and locator forks 152a and 152b prior to injection with follower 154 extended to a selected dosage. Add-on communication module 102 includes housing 108, battery 176, microprocessor circuit board 170, dosage sensor 114, and longitudinal member 154. Dosage sensor 114 is used to measure the injected dose. Longitudinal member 154 moves parallel to the longitudinal axis L2 of the pen, tracking with dosage selector 120 as it moves in and out with an actuation shaft 190 (FIG. 15) of drug delivery pen 124.

Electrical circuit components (not shown due to placement of components in the drawings) are provided on board 170 such as, for example, microprocessor, microcontroller, analog-to-digital converter, speaker, display, memory, display driver, user interface driver, transmitter, receiver or transmitter-receiver (e.g., a wireless transceiver using infrared light, radio-frequency, or optical waves) and antenna to send and receive wireless signals to and from the meter, process input from the sensor, turn the device on and off, put the device into sleep mode, wake the device up, regulate power from battery 176, and store and retrieve information to and from memory, as examples.

As shown in FIG. 15, dosage sensor 114 is preferably a linear potentiometer and is used to measure the position of dosage selector 120 for determining the size of the bolus injected by the user. Sensor 114 is electrically coupled to an analog-to-digital converter, which is coupled to microprocessor board 170 to provide data on the position of dosage selector 120 and dosage actuator 116. A micro-switch (similar to microswitch 268 of FIG. 6) is provided at a position proximate housing end 132 to provide an indication of drug delivery upon button 116 being fully depressed to push shaft 190 towards cartridge 122. Other sensors that may be used with the exemplary embodiments include rotational potentiometers, linear, or rotational encoders. Linear potentiometers are preferred in the operational prototypes built by applicants. However, the embodiments described herein may utilize means for determining displacement of a dosage selector of a drug delivery pen in which the means include a follower, longitudinal member, and a dosage sensor (which may include rotary potentiometer, linear potentiometer, capacitive displacement sensor, optical displacement sensor, magnetic displacement sensor, encoder type displacement sensor, or combinations and equivalents thereof) and equivalents to these components described herein.

Fourth Type Of Add-On Module

Figure 16A:
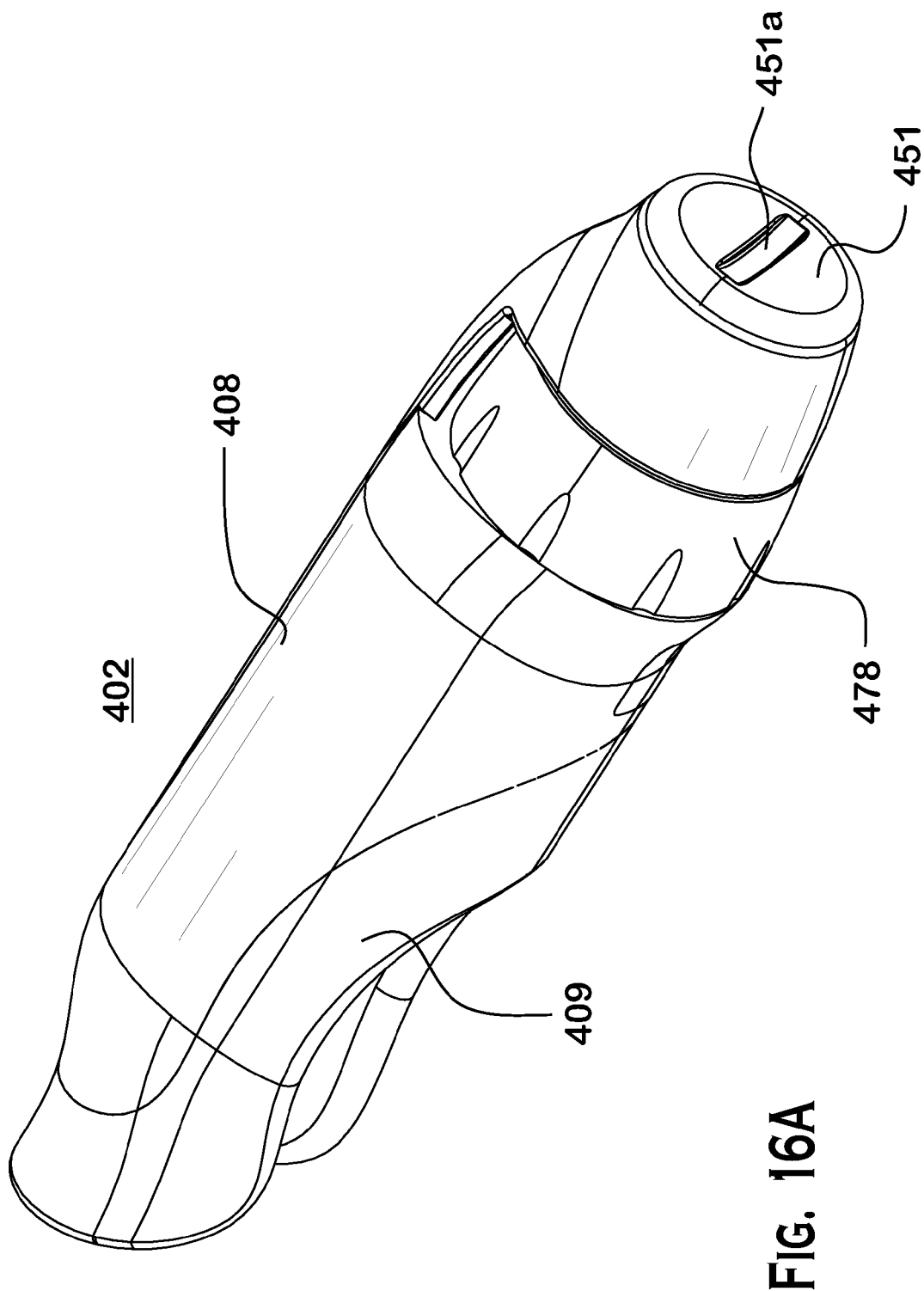
FIG. 16A illustrates a perspective view of yet another type of medical module by itself.
Figure 16B:
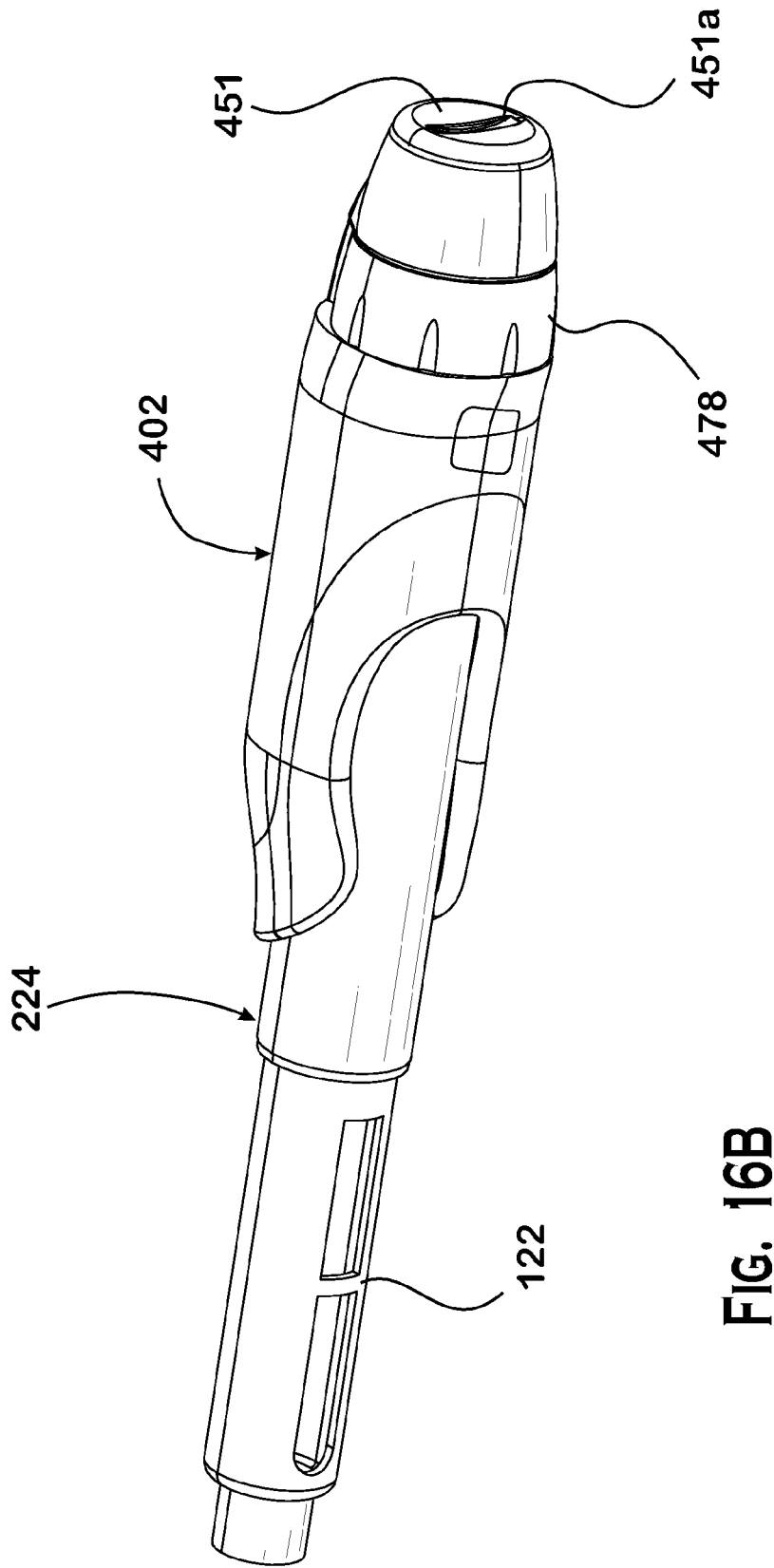
FIG. 16B illustrates a perspective view of the add-on module of FIG. 16A as coupled to a drug delivery pen.

Recognizing that different drug delivery devices (e.g., insulin pens) may be required based on user preferences, applicants have provided for an alternative type of communication module 402, as illustrated in FIG. 16A, which is usable with a drug delivery pen, as illustrated in FIG. 16B. In this embodiment, applicants have provided for an alternative that is designed to further reduce the offset or asymmetric profile. Additionally, applicants have provided for an alternative that has a mechanism for easily changing the batteries. Add-on communication module 402 can include a primary module housing 408, a secondary module housing 409, a rotatable knob 478, a button 451, and a slot 451a. A power supply can be in the form of a disk shape (e.g., coin cell battery) similar in shape to a button 451. The battery can be disposed proximate to button 451 in a stacking relationship.

Slot 451a can be used to rotate button 451 using a coin or screwdriver to easily remove button 451 so that the battery can be changed.

Other Variations Of The Add-On Module

Figure 17A:
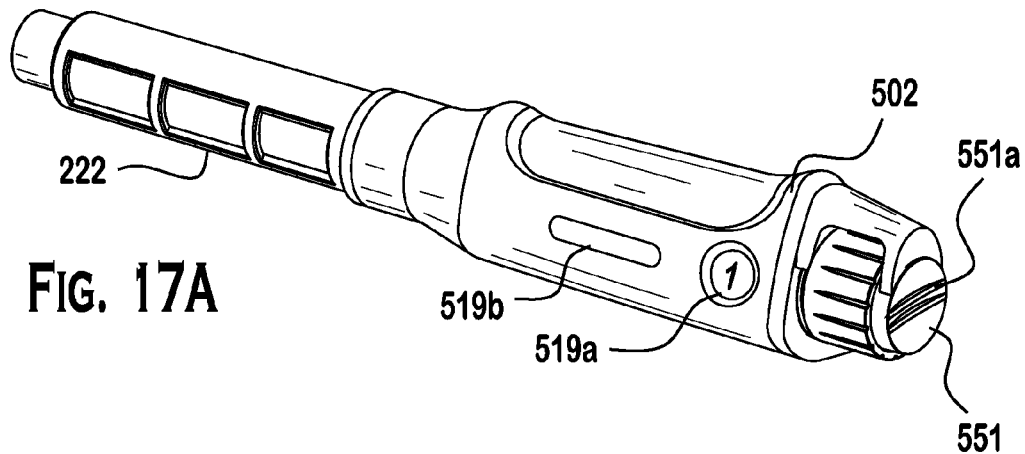
FIGS. 17A, 17B, and 17C illustrate respective variations of the add-on modules described earlier.

FIG. 17A illustrates another embodiment of a communication module 502 that is similar to communication module 102. Add-on communication module 502 does not have a first and second extension portions like communication module 102. Instead, communication module 502 has a housing that wraps around the drug delivery pen. The housing of communication module 502 has two windows 519a and 519b for allowing the user to view display window and written indicia on the pen. Add-on communication module 502 includes a button 551 and a slot 551a. A power supply can be in the form of a disk shape (e.g., coin cell battery) similar in shape to a button 551. The battery can be disposed proximate to button 551 in a stacking relationship. Slot 551a can be used to rotate button 451 using a coin or screw driver to easily remove button 551 so that the battery can be changed.

Figure 17B:
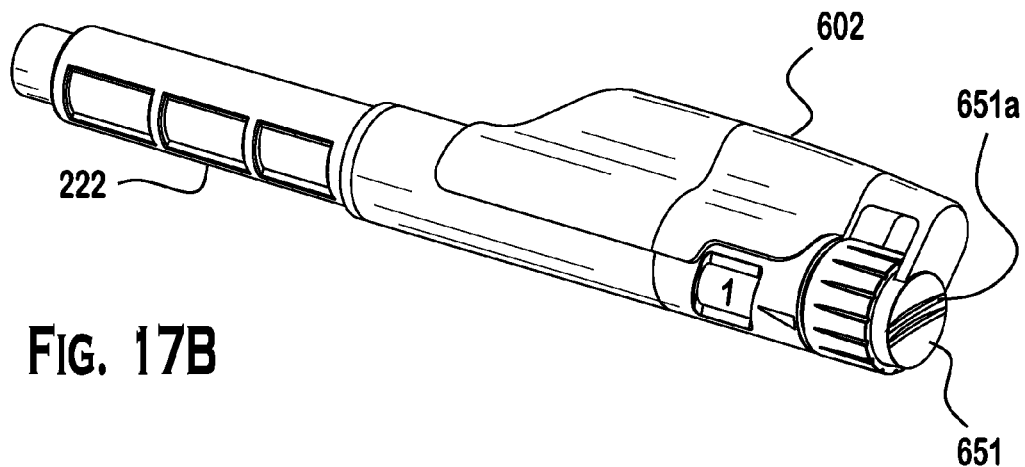

FIG. 17B illustrates another embodiment of a communication module 602 that is similar to communication module 102. Add-on communication module 602 includes a button 651 and a slot 651a that are similar to communication module 502.

Figure 17C:
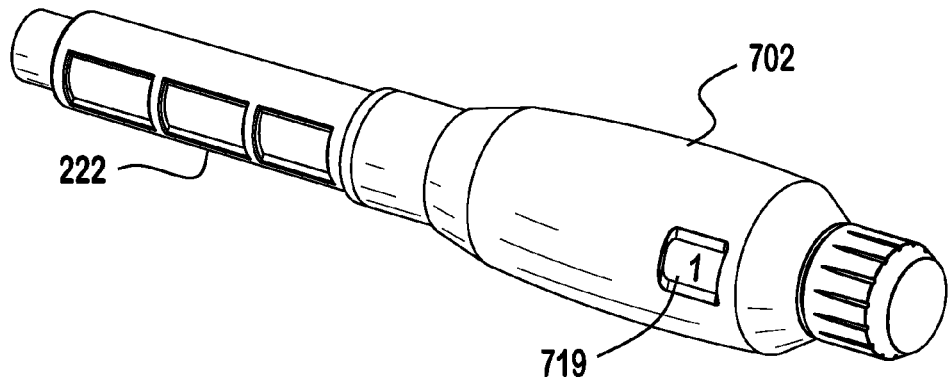

FIG. 17C illustrates another embodiment of a communication module 702 that is similar to communication module 204. In contrast to previous embodiments, communication module 702 has a housing that is symmetrical with respect to a longitudinal axis that extends along the pen. The housing of communication module 702 has a window 719 for allowing the user to view display window on the pen.

OPERATION OF THE EXEMPLARY EMBODIMENTS

In use, a user would couple (e.g., snap-on, slide on, close a clam-shell) the medical module (102, 202, 204, 402, 502, 602, or 702) over actuation end 100 (or 200) of a drug delivery pen 124 (or 224), as shown in FIG. 1, 1B, 8, 10, 11, 11B, 16A, 16B, 17A, 17B, or 17C. Once the medical module (102, 202, 204, 402, 502, 602, or 702) has been coupled to drug delivery pen 124 (or 224), turning dosage selector 120 (or rotating knob 278) allows the user to dial in a dosage for injection. The selected dosage appears in dosage indicator window 118 (or 218) of the pen 124 or 224. As dosage selector 120 rotates, it extends shaft 190 within drug delivery pen 124, illustrated in FIG. 15, causing longitudinal member 154 to extend as well. Similarly, as knob 278 rotates, it extends longitudinal member 254 within the primary module housing 208, as illustrated in FIG. 6. The amount of insulin to be injected is proportional to the extension of shaft 190 (FIG. 15) of pen 124 and longitudinal member 154, which is measured by dosage sensor 114. Similarly, the amount of insulin to be injected is proportional to the extension of follower 240 of module 202 and longitudinal member 254, which is measured by dosage sensor 214. Dosage selector 120 (or knob 278) may be rotated in either direction, increasing or decreasing the selected dosage.

A suitable needle (not shown) can be attached to the insulin cartridge 122 or 222. Before injecting, the user primes drug delivery pen 124 or 224 by ejecting a small dose (typically 2 Units) before inserting a needle subcutaneously. Priming drug delivery pen 124 or 224 eliminates bubbles. While priming, drug delivery pen 124 or 224 should be held with needle pointing upwards. Medical module 102 may distinguish between primes and injections by two exemplary techniques: (1) it may determine via an inertial or acceleration sensor disposed in the housing of the add-on module if drug delivery pen 124 or 224 is held with needle pointing upward (in relation to the ground) during an injection, and (2) it may use software to determine if one or more small doses of approximately 2 Units are followed by a larger dose. In some cases, a separate glucose meter may ask the user to confirm whether a dose was a prime or an injection. In an embodiment, the inertial sensor can also be used to wake up the device if it is in sleep mode when the device is picked up by the user. In the dosing history menu on the glucose meter (not shown), it is possible for the user to toggle entries between prime and injection. As an example, the meter can display primes by indicating with the symbol "*" (for example) which injections were preceded by a prime. Applicant believes that this allows the displaying of as much information as possible on one screen on the meter without confusing the user by showing all the primes and injection doses together in one list.

After dialing in the desired dose, the injection is performed by inserting the needle into the skin and with the user's thumb fully depressing actuation button 116 of pen 124 (for module 102), button 216 of pen 224, or button 251 (for module 202). Once the actuation button is fully depressed, the button must be held down for a predetermined period of time for the selected dosage to be fully injected. As provided in the means for determining dosage injection event and duration thereof, the add-on module records such an event and the duration of the event into its memory. The user may perform this sequence until the cartridge 222 is depleted.

After insulin cartridge 222 is depleted, communication module is removed from disposable drug delivery pen 124 (or 224), disposable drug delivery pen 124 or 224 (e.g., an insulin pen) is thrown away, and communication module 102 is re-attached to a new disposable drug delivery device 124 or 224 (e.g., an insulin pen). Alternatively, where the user is using a reusable pen, the empty drug cartridge could be thrown away and replaced with a new cartridge attached to the actuation portion of the reusable pen.

As noted earlier, the single glucose meter may communicate with multiple medical modules. For example, glucose meter may communicate with a medical module (102, 202, 204, 402, 502, 602, or 702) attached to a rapid acting insulin drug delivery pen and another unit (102, 202, 204, 402, 502, 602, or 702) with a long acting insulin drug delivery pen. Medical modules (102, 202, 204, 402, 502, 602, or 702) may be color coded to match the color of drug delivery pens 124 or 224, identifying the type of insulin that it contains. This feature will help prevent accidental injections of the wrong type of insulin. In an embodiment, the module can be configured to attach to a specific type of pen housing in order to identify the type of insulin. In this embodiment the insulin pen manufacturer provides different type of pen housing shapes for specific types of insulin.

While some features have been described, other variations on the exemplary embodiments may be utilized in various combinations. For example, instead of a potentiometer, the add-on modules may use an encoder to measure angular position and rotation of dosage selector. A switch may be used with the encoder to detect when the user presses on dosage actuation button of the add-on module (102, 202, 204, 402, 502, 602, or 702) to inject a drug, such as, for example, insulin, and allows for differentiation between dosage adjustments and injections. Such switch also detects how long the user continues to press on the dosage actuation button after injecting an insulin shot, as described earlier. In another example, when the switch is activated and after the encoder determines that dosage selector dial has returned to the zero position, the add-on module (102, 202, 204, 402, 502, 602, or 702) may communicate this information to the blood glucose meter to initiate a timer on the meter that counts down the period of time that the user should keep the dial depressed. If the user releases pressure on the switch prematurely, a warning may be announced or displayed on the blood glucose meter. Alternatively or in addition, a small display or LEDs on the snap-on pen module (102, 202, 204, 402, 502, 602, or 702) may be used to cue the user as to how long to press on the dial. It is noted, however, that a display is not absolutely necessary—the device could just track the time that the button is depressed and display a message/warning on the meter if the user does not hold down the button for a sufficient amount of time. The switch may also be configured to work with sensors other than encoders, for example the linear potentiometer as shown exemplarily in FIGS. 1-8. Medical module (102, 202, 204, 402, 502, 602, or 702) 102 may include various features that guide users in the proper use of drug delivery pens 124 or 224. For example, medical module (102, 202, 204, 402, 502, 602, or 702) can: alert the user if they have not primed drug delivery pen 124 or 224 using the inertial sensor; alert the user if a mixing step has not been performed (applicable to mixed insulins) using the inertial sensor; warn the user if the injection is incomplete (i.e., dosage delivery button is not pressed all the way to zero); provide a timer that reminds the user to hold dosage delivery button 116 down for several seconds during an injection; keep track of remaining insulin in drug delivery pen 124 or 224; remind user when it is time to inject; alert the user if injections have been missed or duplicated; alert the user if insulin is about to expire.

In addition, medical module (102, 202, 204, 402, 502, 602, or 702) may include a micro switch in communication module housing 108 to allow for activation of certain features. For example, the insertion of drug delivery pen 124 or 224 into medical module (102, 202, 204, 402, 502, 602, or 702) triggers the micro switch. Triggering the micro switch serves two purposes: first, it signals when a new drug delivery pen 124 or 224 is inserted, which allows medical module (102, 202, 204, 402, 502, 602, or 702) to track how much insulin is left in drug delivery pen 124 or 224; and second, it ensures that drug delivery pen 124 or 224 is inserted correctly, and is properly aligned with medical module.

Another feature that may be included in communication module is a technique for distinguishing a priming dose from a dose that is injected into the user. For example, a gravity or inertial sensor may be used to determine if the device is pointing upwards when dial 3 is pressed, indicating a priming shot since the device is held in an inverted position when purging bubbles. The add-on module is able to distinguish priming shots from actual drug delivery. For example, priming shots are typically two units or less, making them distinguishable from larger injected shots, and a priming shot will typically be followed by an injected shot, a pattern that may be distinguished in software. Similarly, it is useful to be able to distinguish between dosage size adjustments in which the user turns the dial backwards and/or forwards to dial in a specific dosage vs. movement of the dial position from the user injecting a shot. This is detectable by the microcontroller via the dosage sensor as well, since injections into the user should end with the dial returned to the initial, or home position, whereas adjustments of the dial to modify the dosage typically occur when the dial is set at a larger dosage and do not terminate in the initial, or home position of the dial.

Several features may be utilized to reduce inaccuracies in the use of insulin pens. These include missing injections, duplicating injections, and improper priming. Improper priming is especially problematic if a needle (not shown) was left on between doses, allowing air to enter drug cartridge 122. Some insulins, such as 70/30 pre-mix, must be mixed prior to injection. Neglecting to mix or improperly mixing 70/30 pre-mix before injection is a source of inaccuracy. Dosage delivery button 116 should be held for approximately 6 seconds during an injection to ensure the entire dose enters the body. Not holding dosage delivery button 116 long enough results in a partial dose. Medical module alerts the user to these inaccuracies and thus helps to reduce them.

As mentioned previously, the medical module (102, 202, 204, 402, 502, 602, or 702) may be used to measure insulin doses and transfer that information to a data management unit, which may be a glucose meter or a suitable data communication unit such as a mobile phone, insulin pump, or controller. The information that is transferred from medical module to the data management unit may be used to help master the use of drug delivery pen 124 or 224. Large potential sources of inaccuracy in the use of drug delivery pen 124 or 224 are missed doses and double doses. Medical module, as embodied herein, may help eliminate these sources of error by reminding the user of their dosing history. The complete dosing history (including doses and time and date the doses were delivered) may be made available to the user by selecting this option from the data management unit's menu. In addition, by having the most recent dosing information (time and amount) on a meter's display when the data management unit turns on, the user will immediately see if they have forgotten an injection every time they take a blood glucose measurement. In the same way that a data management unit may be used to alert a user when it's time to test blood glucose, the data management unit may also alert the user when to take insulin, or if an insulin injection has been missed. This information may also be displayed when the data management unit turns on.

Another source of inaccuracy when using drug delivery pens 124 or 224 is improper priming technique (or failing to prime altogether). The purpose of priming (sometimes called a test injection) is to remove air bubbles from drug cartridge 122 and needle, which would reduce the volume of an injection. Drug delivery pen 124 or 224 should be held vertically during priming so bubbles rise to the top of drug cartridge 122 (the end closest needle) and may be expelled by a priming dose. The priming is successful if the user sees a drop of insulin appear at the needle tip. If the user does not see a drop of insulin, the priming step is repeated. An inertial sensor is disposed in the module housing or located on the processor board 170 or 270 to detect if drug delivery pen 124 or 224 is held vertically during priming, and this information may be sent wirelessly to the data management unit. Low cost microelectromechanical systems (MEMS) inertial sensor chips are widely available, accurate, low cost, and small in size. Preferred inertial sensor may include Analog Devices model ADXL322 accelerometer (available at http://www.analog-.com/en/mems-and-sensors/imems-accelerometers/ADXL322/products/product.html#pricing). The data management unit may remind the user to hold drug delivery pen 124 or 224 vertically when priming, if they are not doing so. In addition, if the user skips the priming step altogether, this will be apparent from the information collected by medical module 102, 202, or 204, and a visual or auditory warning, reminder, and/or instructions may be given to the user by the add-on module or the data management unit.

The inertial sensor is also utilized to determine if the user is performing the proper mixing technique before injecting insulin, another source of error in using drug delivery pen 124 or 224. Some insulins must be mixed prior to use, such as 70/30 pre-mixed insulin. Mixing typically involves moving drug delivery pen 124 or 224 from straight up to straight down ten times, an action that is easily detectable by an inertial sensor (located in an attached medical module 102, 202, or 204. A message may be displayed on the data management unit to remind the patient how to mix their insulin if they are using insulin that requires mixing prior to use.

Another source of error related to priming is that of neglecting to remove and dispose of needles after each injection. The meter, in one embodiment, would provide a display to generate a reminder stating that the needle should be removed with every use. Alternatively, the speaker mounted in the add-on module can be utilized to prompt the user with tones or prestored phrases configured for specific geographical areas (e.g., German for modules distributed in Germany, French for modules distributed in France and so on). Additionally, the speaker in the add-on module may be configured to allow a user to locate a misplaced pen and module. Specifically, the add-on module may respond to an inquiry signal from a data management unit (or any electronic devices paired to the add-on module) to cause the speaker in the add-on module to emit tones or beeps in the event that the user has misplaced the pen and module. This method also can be used to confirm that a particular communication module is paired with a particular data management unit such as a glucose meter.

When injecting insulin with drug delivery pen 124 or 224, it is important to hold down on dosage delivery button 116 with needle inserted for approximately six seconds, to ensure that the entire dose is delivered below the skin. The optimal amount of time is usually spelled out in drug delivery pen 124 or 224 user's manual. A message may be displayed on either or both of the add-on module or the data management unit, reminding the user of proper technique if they are releasing dosage delivery button 116, 216 or 251 prematurely. The data management unit or the add-on module may display a countdown timer or emit a countdown tone or signals, initiated when dosage delivery button 116 is first pressed, letting the user know when they should release dosage delivery button 116.

Other pen-related usage reminders, such as the amount of time a pen may be used after removed from refrigeration, also may be incorporated into the smart pen module and displayed on the blood glucose meter as an aide to the user. To track the time a particular pen has been in use, the user would need to indicate the initiation of a new pen on the meter. In such embodiment, a switch is provided in the hollow bore of the smart pen module that is activated when it is attached to a pen, signaling the initiation of a new pen. The user may be asked to confirm on the meter when a new pen is initiated by pressing a button and possibly entering some information, such as the amount of insulin in the new pen.

In the examples given above, the add-on module (102, 202, 204, 402, 502, 602, or 702) is provided with a transceiver to allow receipt and transmission of information collected by the smart pen module to a cell phone or computer for easy look up or prominent display.

These features described and illustrated may be incorporated into a re-usable pen, in addition to a conventional disposable pen.

To our knowledge, no other device has sought to address the problems recognized here by applicants, with the exception of conventional digital insulin pens that display the last few injection amounts.

Several prototypes have been built that measure the amount of each dose and transmit this information to a meter for display. During evaluation of the prototypes, it was recognized by applicants that it would be useful to have the device communicate with multiple pens, since users often use one pen for long acting insulin and a separate pen for rapid acting insulin. In addition, some patients use more than one pen of the same type of insulin, placing them in different convenient locations (for example, at home, at work, in the car, etc.). Hence, applicants have realized that multiple communication modules may communicate with the data management unit (e.g., analyte meter, infusion pump or controller) for each of these pens to ensure that all insulin injections are captured. Also, it was further realized by applicants that the communication modules may be color-coded so that they would match the color of the drug delivery pen they are designed to work with. This feature is believed to be useful to users because insulin companies use the same pen to deliver different insulins, and they use color-coding to help the users distinguish between different pens. The communication modules may alert the user via a message, visual warning, or alarm on the add-on module(s) or meter as to the type of insulin they are injecting, helping them catch a potential error in which they might be injecting the wrong insulin—an error that may cause hypoglycemia or hyperglycemia.

While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well.

What is claimed is:

1. A drug delivery system comprising:
   a drug delivery pen having a generally tubular pen housing that extends from a first end to a second end, the first end of the pen housing enclosing at least a portion of a plunger rod coupled to a drug cartridge disposed proximate the second end of the pen housing, the first end of the pen housing having a dosage selector coupled to the plunger rod;
   an add-on module housing extending along a first longitudinal axis from a first add-on module housing end to a second add-on module housing end, the add-on module housing including first and second extensions that partially circumscribe a portion of the first end of the pen housing for attachment of the add-on module housing to the drug delivery pen; and
   a dosage sensor coupled to the add-on module housing and located on one side of the first longitudinal axis,
   in which the dosage sensor includes a longitudinal member movable along the longitudinal axis, the longitudinal member connected to a follower portion that extends from the add-on module housing proximate the second add-on module housing end;
   a power source coupled to the add-on module housing, located on another side of the first longitudinal axis and spaced apart from the dosage sensor; and
   a micro-controller disposed in the add-on module housing proximate the first longitudinal axis and located between dosage sensor and the power source.

2. A drug delivery system comprising:
   a drug delivery pen having a generally tubular pen housing that extends from a first end to a second end, the first end of the pen housing enclosing at least a portion of a plunger rod coupled to a plunger disposed in a drug cartridge located proximate the second end of the pen housing, the first end of the pen housing having a dosage selector coupled to the plunger rod;

an add-on module housing having a primary communication module housing extending along a first longitudinal axis from a first communication module housing end to a second communication module end, in which the primary module housing includes:
   a dosage sensor coupled to the primary communication module housing;
   a follower portion connected to the dosage sensor and disposed for movement relative to the primary communication module housing; and
   retention forks connected to the follower portion, the retention forks configured to capture a button of the dosage selector between the retention forks; and
a secondary communication module housing coupled to the primary housing module, the secondary communication module extending along a second axis to define at least a portion of a hollow bore, the at least a portion of a hollow bore configured for attachment over an actuation unit of a drug delivery pen.

3. A drug delivery system comprising:
a drug delivery pen having a generally tubular pen housing that extends from a first end to a second end, the first end of the pen housing enclosing at least a portion of a plunger rod coupled to a plunger disposed in a drug cartridge located proximate the second end of the pen housing, the first end of the pen housing having a dosage selector coupled to the plunger rod; and an add-on module housing extending along a longitudinal axis from a first add-on module housing end to a second add-on module housing end to define at least a portion of a hollow bore in which the hollow bore is configured for attachment over at least a portion of the first end of the drug delivery pen;

a casing connected to the add-on module housing and configured to enclose a portion of an outer surface of the add-on module housing, the casing being located asymmetrically with respect to the longitudinal axis to house electrical components;

a dosage sensor disposed in the casing located on one side of the first longitudinal axis in which the dosage sensor includes a longitudinal member movable along the longitudinal axis, the longitudinal member connected to a follower portion that extends from the add-on module housing proximate the second add-on module housing end;

a power source coupled to the add-on module housing, located on another side of the first longitudinal axis and spaced apart from the dosage sensor;

a micro-controller disposed in the add-on module housing proximate the first longitudinal axis;

a follower portion physically connected to the dosage sensor and disposed for movement relative to the add-on module housing; and a knob mounted to the add-on module housing and physically connected to the dosage sensor via the follower portion so that a portion of the dosage sensor is movable in proportion to movement of the knob along the longitudinal axis.

4. The drug delivery system of claim 3, further comprising respective first and second locating tangs, each locating tang protrudes beyond each of the first and second extensions to locate the add-on module housing to the dosage indicator window.

5. The drug delivery system of one of claim 1, 2, or 3, in which the micro-controller comprises:
   a memory;
   a processor coupled to the memory;
   an analog-to-digital converter coupled to the dosage sensor and the processor so as to provide data on displacement of a movable follower; and
   a transceiver to transmit and receive data stored in memory.

6. The drug delivery system of one of claim 1, 2, or 3, in which the drug delivery pen comprises a disposable insulin pen.

7. The drug delivery system of one of claim 1, 2, or 3, in which the drug deliver pen comprises a reusable insulin pen.

8. The drug delivery system of one of claim 2, or 3, in which the dosage sensor is selected from a group consisting of resistance, capacitance, optical, magnetic or combination thereof.

9. The drug delivery system of one of claim 2, or 3, further comprising an inertial sensor disposed in the add-on module housing to determine the orientation of the drug cartridge.

10. The drug delivery system of one of claim 2, or 3, further comprising a micro-switch disposed in the add-on module housing to allow a determination of at least one of replacement or position of the drug delivery pen.

11. The drug delivery system of one of claim 1, 2, or 3, in which the drug cartridge contains a drug selected from a group consisting essentially of long acting insulin, rapid acting insulin, long and rapid acting mixed insulin, NPH, growth hormone, GLP-1 analogs, Symlin, or combinations thereof.

12. The drug delivery system of one of claim 1, 2, or 3, further comprising a proximity detector disposed on an inner surface of the hollow bore to allow a determination of replacement of the drug delivery pen when the pen is inserted or removed from the hollow bore.

13. The drug delivery system of claim 12, in which the proximity detector is selected from a group consisting of an optical detector, ultrasound detector, mechanical detector, or combinations thereof.

14. The drug delivery system of claim 12, in which the longitudinal member comprises a slider disposed on a potentiometer, the slider being slidable on the potentiometer along the longitudinal axis between proximate the first housing end and the second housing end upon movement of the knob.

15. The drug delivery system of claim 14, further comprising a switch disposed proximate the first housing end, the switch configured to respond as a momentary switch upon the knob being moved towards a terminal position proximate the second housing end.

16. The drug delivery system of one of claim 1, 2, or 3, in which the microcontroller comprises:
   a memory;
   a microprocessor coupled to the memory;
   an analog-to-digital converter coupled to the dosage sensor and the microprocessor so as to provide data on displacement of a follower portion; and
   a transmitter to transmit data stored in memory.

17. The drug delivery system of claim 16, further comprising an inertial sensor disposed in the housing to allow for determination of mixing or priming of the drug delivery pen.

18. The drug delivery system of claim 16, further comprising a micro switch disposed in the hollow bore to provide a signal to the microcontroller indicative of insertion and removal of a drug delivery pen.

19. The drug delivery system of claim 16, in which the dosage sensor is selected from a group consisting of a rotary potentiometer, linear potentiometer, capacitive displacement sensor, optical displacement sensor, magnetic displacement sensor, encoder type displacement sensor, or combination thereof.

20. The drug delivery system of one of claim 1, 2, or 3, further comprising an inertial sensor disposed in the communication module housing to determine the orientation of the drug cartridge.

21. A drug delivery system comprising:
- a drug delivery pen having a generally tubular pen housing that extends from a first end to a second end, the first end of the pen housing enclosing at least a portion of a plunger rod coupled to a plunger disposed in a drug cartridge located proximate the second end of the pen housing, the first end of the pen housing having a dosage selector coupled to the plunger rod; and
- an add-on module configured to attach to the drug delivery pen proximate the first end of the pen housing, the module including:
  - a module housing extending along a longitudinal axis from a first module housing end to a second module housing end to define at least a portion of a hollow bore disposed about the longitudinal axis in which the hollow bore is configured to couple over a portion of the first end of the pen housing; and
  - a casing connected to the module housing to enclose a portion of an outer surface of the module housing, the casing including means for determining either one of a dosage delivery or duration of dosage delivery or both upon actuation of the pen by a user.

* * * * *